United States Patent
Bruehwiler et al.

(10) Patent No.: US 9,408,980 B2
(45) Date of Patent: Aug. 9, 2016

(54) DUAL-CHAMBERED DRUG DELIVERY DEVICE FOR HIGH PRESSURE INJECTIONS

(75) Inventors: Michel Bruehwiler, Newton, MA (US); Melissa Rosen, Lynn, MA (US); Ryan Schoonmaker, Salem, MA (US); Ira Spool, Brookline, MA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 1105 days.

(21) Appl. No.: 12/998,853

(22) PCT Filed: Dec. 8, 2009

(86) PCT No.: PCT/US2009/006420
§ 371 (c)(1),
(2), (4) Date: Sep. 20, 2011

(87) PCT Pub. No.: WO2010/077278
PCT Pub. Date: Jul. 8, 2010

(65) Prior Publication Data
US 2012/0004641 A1    Jan. 5, 2012

Related U.S. Application Data

(60) Provisional application No. 61/193,593, filed on Dec. 9, 2008.

(51) Int. Cl.
*A61M 5/315* (2006.01)
*A61M 5/19* (2006.01)
(Continued)

(52) U.S. Cl.
CPC .............. *A61M 5/31553* (2013.01); *A61M 5/19* (2013.01); *A61M 5/204* (2013.01); *A61M 5/31511* (2013.01); *A61M 5/484* (2013.01); *A61M 2005/3128* (2013.01)

(58) Field of Classification Search
CPC .... A61M 5/19; A61M 5/204; A61M 5/31553
USPC .......................................... 604/191, 211, 247
See application file for complete search history.

(56) References Cited

U.S. PATENT DOCUMENTS

| 3,572,556 A | * | 3/1971 | Pogacar ................. A61M 5/484 222/309 |
| 4,643,723 A | * | 2/1987 | Smit ..................... A61M 5/204 604/207 |

(Continued)

FOREIGN PATENT DOCUMENTS

| JP | 2001501504 A | 2/2001 |
| JP | 2006526467 A | 11/2006 |
| WO | WO-9811926 A1 | 3/1998 |

OTHER PUBLICATIONS

Office Action Dated Nov. 26, 2013 Issued in Japanese Patent Application No. 2011-540687.

*Primary Examiner* — Kami A Bosworth
(74) *Attorney, Agent, or Firm* — Dickinson Wright PLLC

(57) ABSTRACT

A dual-chambered drug delivery device (201) includes a first chamber (205) in which a medicament is stored. A dose setting member (213) is rotated to set a medicament dose. The dose setting member (213) being rotatable to set the medicament dose. The dose setting member (213) is not axially moveable. A second chamber (221) is in fluid communication with the first chamber (205). The medicament dose is transferred to the second chamber (221) from the first chamber (205) prior to injecting the medicament dose. A needle (203) communicates with the second chamber (221) to inject the medicament dose into an injection site.

18 Claims, 37 Drawing Sheets

(51) Int. Cl.
   *A61M 5/20*   (2006.01)
   *A61M 5/48*   (2006.01)
   *A61M 5/31*   (2006.01)

(56) References Cited

U.S. PATENT DOCUMENTS

| | | | |
|---|---|---|---|
| 4,755,169 A | | 7/1988 | Sarnoff |
| 5,279,585 A | | 1/1994 | Balkwill |
| 5,279,586 A | | 1/1994 | Balkwill |
| 5,298,023 A | | 3/1994 | Haber |
| 5,456,672 A | | 10/1995 | Diederich |
| 5,505,704 A | | 4/1996 | Pawelka |
| 5,549,575 A | | 8/1996 | Giambattista |
| 5,569,214 A | | 10/1996 | Chanoch |
| 5,575,280 A | | 11/1996 | Gupte |
| 5,582,598 A | | 12/1996 | Chanoch |
| 5,674,204 A | | 10/1997 | Chanoch |
| 5,843,042 A | * | 12/1998 | Ren ............ A61J 1/20 604/207 |
| 5,921,966 A | | 7/1999 | Bendek |
| 5,944,700 A | | 8/1999 | Nguyen |
| 5,957,896 A | | 9/1999 | Bendek |
| 6,056,728 A | | 5/2000 | von Schuckmann |
| 6,074,372 A | | 6/2000 | Hansen |
| 6,096,010 A | | 8/2000 | Walters |
| 6,221,053 B1 | | 4/2001 | Walters |
| 6,248,095 B1 | | 6/2001 | Giambattista |
| 6,277,099 B1 | | 8/2001 | Strowe |
| 6,537,242 B1 | | 3/2003 | Palmer |
| 6,652,483 B2 | | 11/2003 | Slate |
| 6,689,101 B2 | | 2/2004 | Hjertman |
| 6,932,794 B2 | | 8/2005 | Giambattista |
| 6,936,032 B1 | | 8/2005 | Bush, Jr. |
| 6,986,758 B2 | | 1/2006 | Schiffmann |
| 7,018,364 B2 | | 3/2006 | Giambattista |
| 7,056,307 B2 | * | 6/2006 | Smith et al. ............ 604/207 |
| 7,104,972 B2 | | 9/2006 | Moller |
| 7,169,132 B2 | | 1/2007 | Bendek |
| 7,217,253 B2 | | 5/2007 | Slate |
| 7,278,985 B2 | * | 10/2007 | Agerup ............ 604/191 |
| 2001/0037087 A1 | * | 11/2001 | Knauer ............ 604/137 |
| 2002/0007142 A1 | * | 1/2002 | Hjertman ............ A61M 5/30 604/38 |
| 2003/0050602 A1 | | 3/2003 | Pettis et al. |
| 2006/0229562 A1 | | 10/2006 | Marsh et al. |
| 2007/0060894 A1 | | 3/2007 | Dai |
| 2007/0197976 A1 | | 8/2007 | Jacobs |

* cited by examiner

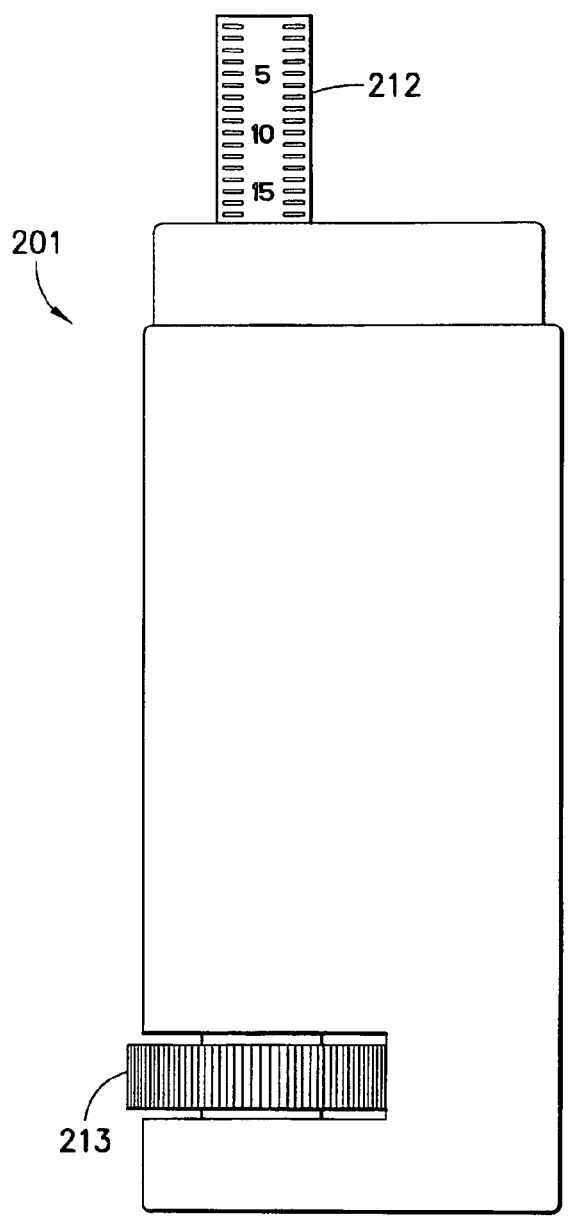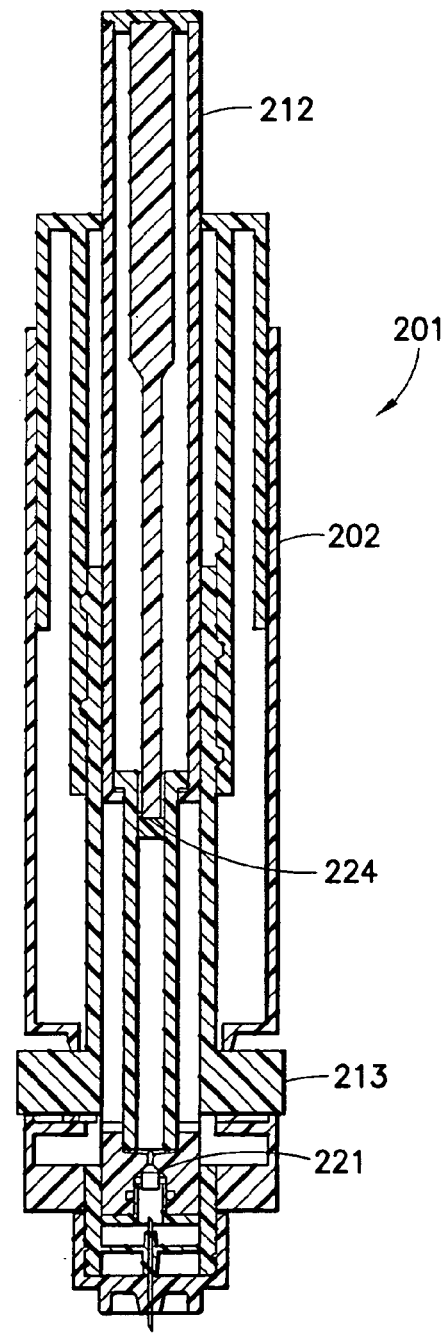
FIG.6
FIG.7

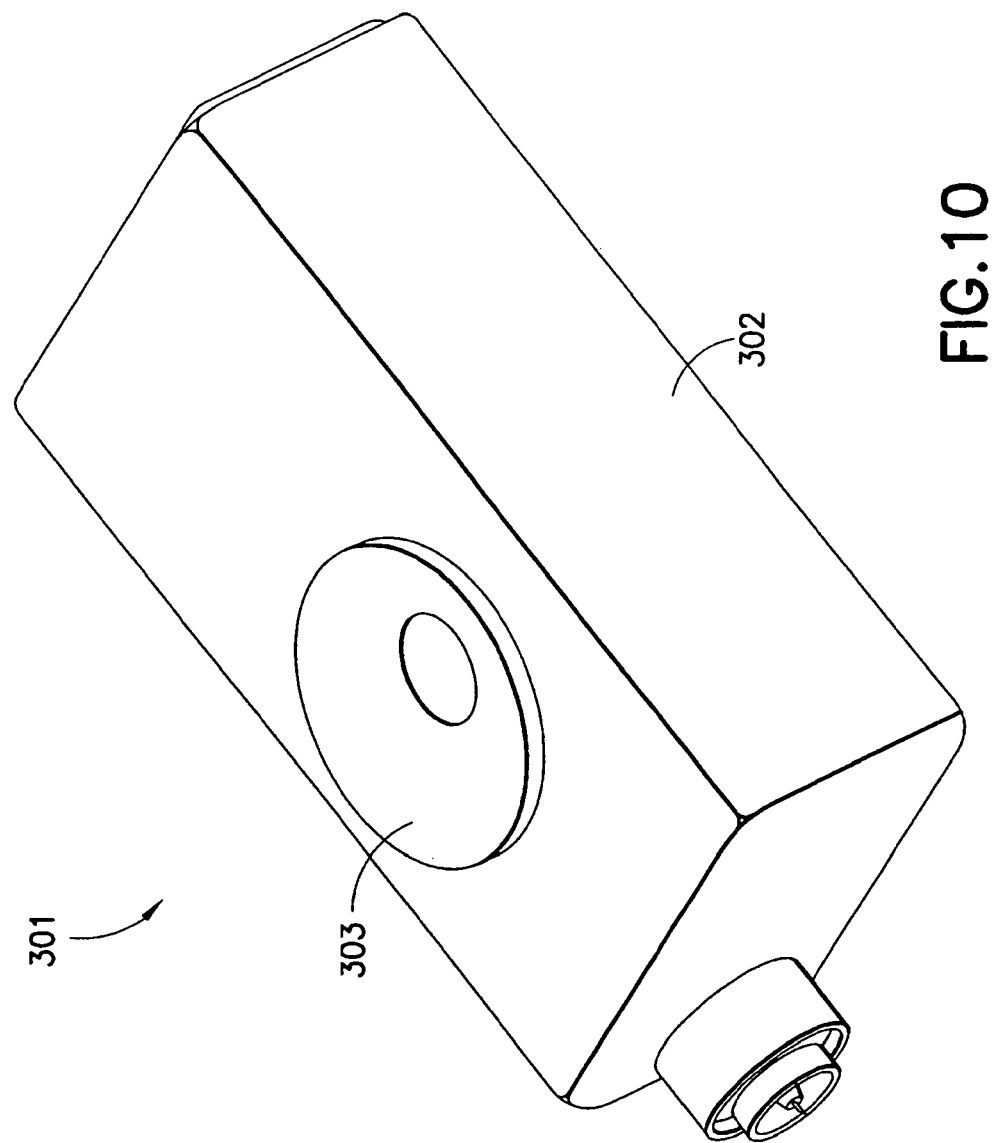

DUAL-CHAMBERED DRUG DELIVERY DEVICE FOR HIGH PRESSURE INJECTIONS

CROSS REFERENCE TO RELATED APPLICATION

This application claims the benefit under 35 U.S.C. §119 (e) of U.S. Provisional Application Ser. No. 61/193,593, filed Dec. 9, 2008, the entire content of which is hereby incorporated by reference.

FIELD OF THE INVENTION

The present invention relates generally to a drug delivery device that facilitates high pressure medication injections. More particularly, the present invention relates to a drug delivery device that diverts high pressures away from the original drug container to prevent medication leakage and inaccurate doses. Still more particularly, the present invention relates to a drug delivery device having a secondary chamber that amplifies the injection force, thereby facilitating intradermal medication injections.

BACKGROUND OF THE INVENTION

Insulin and other injectable medications are commonly given with syringes into the intradermal layer of the skin and other dense tissues. Intradermal medication injections result in faster uptake of the medication, thereby resulting in improved therapy. Such injections require higher injection pressures, upwards of 200 psi, than traditional subcutaneous injections.

Techniques and devices are known for administering an injection into the intradermal region of the skin. One method, commonly referred to as the Mantoux technique, uses a "standard" needle and syringe, i.e., a syringe typically used to administer intramuscular or subcutaneous injections. The health care provider administering the injection follows a specific procedure that requires a somewhat precise orientation of the syringe with regard to the patient's skin as the injection is administered. The health care provider must also attempt to precisely control the penetration depth of the needle into the patient's skin to ensure that it does not penetrate beyond the intradermal region. Such a technique is complicated, difficult to administer, and often may only be administered by an experienced health care professional.

A conventional syringe 101 is shown in FIG. 1. The needle 103 is sufficiently long to deliver the drug to the subcutaneous region of the skin. However, a user would not be able to easily deliver the medicament to the intradermal region of the skin, as discussed above.

Existing drug delivery pens offer several advantages over syringe-based systems for delivering insulin subcutaneously. Reusable drug delivery pens hold 20 or more doses without requiring the drug cartridge to be refilled. Dose setting is achieved simply with the use of a dial. However, those injection systems are designed for low pressure subcutaneous injections. Intradermal injection of insulin and other medications provides faster uptake of the drug, thereby leading to improved therapy. Existing drug delivery pens have several limitations regarding intradermal drug delivery. First, the mechanical advantage provided by the pen is minimal and requires the user to supply upwards of 20 lbs of force to generate sufficient pressure. Second, the pen components can be damaged by this high force, resulting in leaking and inaccuracy at the high pressures.

Drug delivery pens, such as the exemplary drug delivery pen 100 shown in FIGS. 2 and 3, are designed for subcutaneous injections and typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is used by the user to securely hold the drug delivery pen 100 in a shirt pocket, purse or other suitable location and provide cover/protection from accidental needle injury.

FIG. 3 is an exploded view of the drug delivery pen 100 of FIG. 2. The dose knob/button 24 has a dual purpose and is used both to set the dosage of the medication to be injected and to inject the dosed medicament via the leadscrew 7 and stopper 15 through the medicament cartridge 12, which is attached to the drug delivery pen through a lower housing 17. In standard drug delivery pens, the dosing and delivery mechanisms are all found within the outer sleeve 13 and are not described in greater detail here as they are understood by those knowledgeable of the prior art. The distal movement of the plunger or stopper 15 within the medicament cartridge 12 causes medication to be forced into the needle 11 of the hub 20. The medicament cartridge 12 is sealed by septum 16, which is punctured by a septum penetrating needle cannula 18 located within the hub 20. The hub 20 is preferably screwed onto the lower housing 17, although other attachment means can be used, such as attaching to the cartridge. To protect a user, or anyone who handles the pen injection device 100, an outer cover 69, which attaches to the hub 20, covers the hub. An inner shield 59 covers the patient needle 11 within the outer cover 69. The inner shield 59 can be secured to the hub 20 to cover the patient needle by any suitable means, such as an interference fit or a snap fit. The outer cover 69 and the inner shield 59 are removed prior to use. The cap 21 fits snugly against outer sleeve 13 to allow a user to securely carry the drug delivery pen 100.

The medicament cartridge 12 is typically a glass tube sealed at one end with the septum 16 and sealed at the other end with the stopper 15. The septum 16 is pierceable by a septum penetrating cannula 18 in the hub 20, but does not move with respect to the medicament cartridge 12. The stopper 15 is axially displaceable within the medicament cartridge 12 while maintaining a fluid tight seal.

The backpressure in subcutaneous injections is not very large, while the backpressure associated with intradermal injections may be many times greater than that of subcutaneous injections. Existing drug delivery pens require a large force to inject medication into the intradermal layer, thereby making the intradermal medication injection difficult. For example, the backpressure often exceeds 200 psi for an intradermal injection, while the backpressure for a subcutaneous injection is generally in the range of 30-50 psi. Thus, a need exists for a drug delivery pen that provides a mechanical advantage to facilitate an injecting a medicament dose intradermally. Furthermore, the drug delivery pen components can be damaged due to the high pressures associated with intradermal injections, thereby resulting in medication leakage and dose inaccuracy.

SUMMARY OF THE INVENTION

In accordance with an aspect of the present invention, a drug delivery device is provided that facilitates injecting insulin or other medicaments at high pressures.

In accordance with another aspect of the present invention, a drug delivery device has a second chamber that amplifies the injection force, thereby facilitating intradermal medication injections.

In accordance with yet another aspect of the present invention, high pressures associated with intradermal injections are diverted from the original medicament container to substantially prevent medication leakage and inaccurate doses.

In accordance with another aspect of the present invention, a drug delivery device has a dose limiter that prevents a user from dialing a dose that is greater than the available medicament.

The drug delivery device operates by transporting a bolus of medication from a primary container (or cartridge) to a secondary chamber using a fluid channel and a compression spring, thereby resulting in a positive pressure differential between the cartridge and the secondary chamber. The secondary chamber employs a smaller cross sectional area than the original medicament container to amplify injection pressure at a given input force on a plunger rod. In the ready state, the secondary chamber contains a full bolus (or maximum dose). The user then dials a desired dose that in turn moves a dose setter relative to the plunger rod to indicate the number of units. After the needle is inserted, the plunger rod is depressed to inject the dialed dose into the patient.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying drawing figures, in which:

FIG. 6 is a front elevational view of the drug delivery device of FIG. 4;

FIG. 7 is a side elevational view in cross section of the drug delivery device of FIG. 4;

FIG. 10 is a perspective view of a drug delivery device according to a second exemplary embodiment of the present invention;

Throughout the drawings, like reference numbers will be understood to refer to like parts, components and structures.

DETAILED DESCRIPTION OF THE EXEMPLARY EMBODIMENTS

Figure 1:
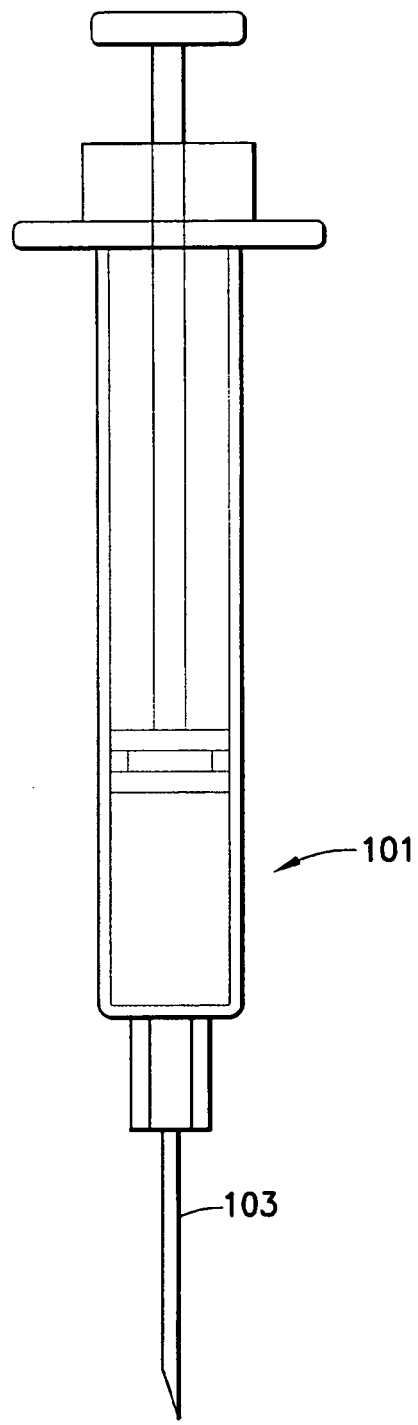
FIG. 1 is a front elevational view of a syringe.
Figure 2:
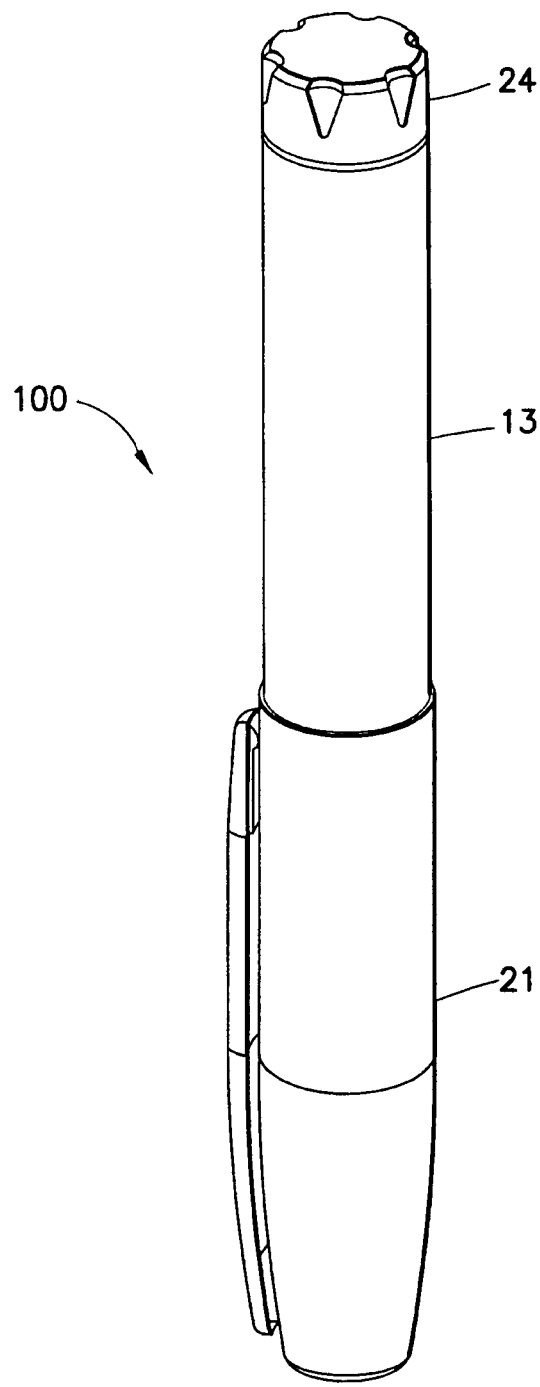
FIG. 2 is a perspective view of a drug delivery pen.

The drug delivery device according to exemplary embodiments of the present invention allows the user to inject medication at high pressures with lower input forces by decoupling the primary (original) drug container or cartridge and its cross sectional area from the injection mechanics.

The drug delivery device has advantages in improved dose accuracy and reduced medicament leakage over existing drug delivery pens by diverting high pressures away from the cartridge, particularly the cartridge stopper. At high pressures, the cartridge stopper can deform, which can change the delivery volume and result in dose inaccuracies. Additionally, when the cartridge stopper is allowed to equilibrate and return to its natural volume after the needle is removed from the intradermal space and the back pressure dissipates, unwanted expulsion of the medicament can occur.

In an exemplary embodiment of the present invention shown in FIGS. 4-9, a drug delivery device 201 injects insulin or other medicaments at high pressures. A first chamber 205 of a cartridge 211 and a second chamber 221 are disposed in a device housing 202. A needle hub 204 is connected to the housing 202. A needle 203 is rigidly fixed in the needle hub 204 and communicates with the second chamber 221. Preferably, the needle 203 is an intradermal needle. Alternatively, the needle may be a subcutaneous needle. Preferably, the needle is a small gauge needle, such as a 34 gauge needle. The drug delivery device according to exemplary embodiments of the present invention injects insulin, high viscosity medicaments, or other medicaments at high pressures.

A bolus of medication is transported from the first chamber 205 of the primary container (or cartridge) 211 to the second chamber 221 using a fluid channel 231 and a compression spring 222, thereby resulting in a positive pressure differential between the cartridge 211 and the second chamber 221. The second chamber 221 employs a smaller cross sectional area than the first chamber 205 of the cartridge 211 to amplify injection pressure at a given input force on a plunger rod 212. The compression spring 222 extends between a spring housing 223 and a stopper 215 disposed in the cartridge 211. The spring housing 223 extends externally of the device housing 202 such that the spring housing 223 is accessible by the user.

In the ready state, the second chamber 221 contains a full bolus (or maximum dose). The user then dials a desired dose on a dose wheel 213 that in turn moves a dose setter relative to the plunger rod 212 to indicate the number of units. The size of the dialed dose may be indicated on the plunger rod 212. After the needle 203 is inserted, the plunger rod 212 is depressed to inject the dialed medicament dose into the patient. The drug delivery device 201 diverts the high pressure from the first chamber 205 of the cartridge 211 to prevent medication leakage and inaccurate doses. As shown in FIG. 6, a longitudinal axis through the center of the dose setting wheel 213 is substantially parallel to a direction of travel of the plunger rod 212.

As shown in FIGS. 4-9, the injection pressure is decoupled from the cartridge 211 by moving the medicament to a second chamber 221 via a conduit (fluid channel) 231 using a pressure (created by the user input force that releases the compression spring 222) in the cartridge 211 and a two-valve system for injecting the dialed dose from the secondary chamber 221 into the patient. The first valve 214 opens to allow the second chamber 221 to fill while the second valve 216 is closed. During injection, the first valve 214 closes and the second valve 216 opens to allow the medicament dose to be injected. The second chamber 221 has a smaller cross sectional area than the first chamber 205 of the cartridge 211 thus providing higher pressure with the same user input force. Using the relationship of pressure, force and area, P=F/A, a second chamber 221 with half the cross sectional area of the first chamber 205 produces twice the pressure at a given load.

Improved dose accuracy and reduced "drooling" problems related to cartridge stopper effects under high pressure are obtained by decoupling the high injection pressure from the primary drug container (cartridge) 211 and into a less-pressure sensitive (in terms of deformation) second chamber 221 and stopper 224.

Further, dose accuracy is higher than that of existing drug delivery pens as the travel distance of the plunger rod stopper 224 to deliver 1 unit of medication out of the smaller second chamber 221 is approximately 1 mm when compared to the approximately 0.15 mm travel distance of the cartridge stopper 215 to deliver 1 unit out of the larger first chamber 205 of the cartridge 211. This improved dose accuracy over existing drug delivery pens is significant, particularly at low dose ranges.

Figure 3:
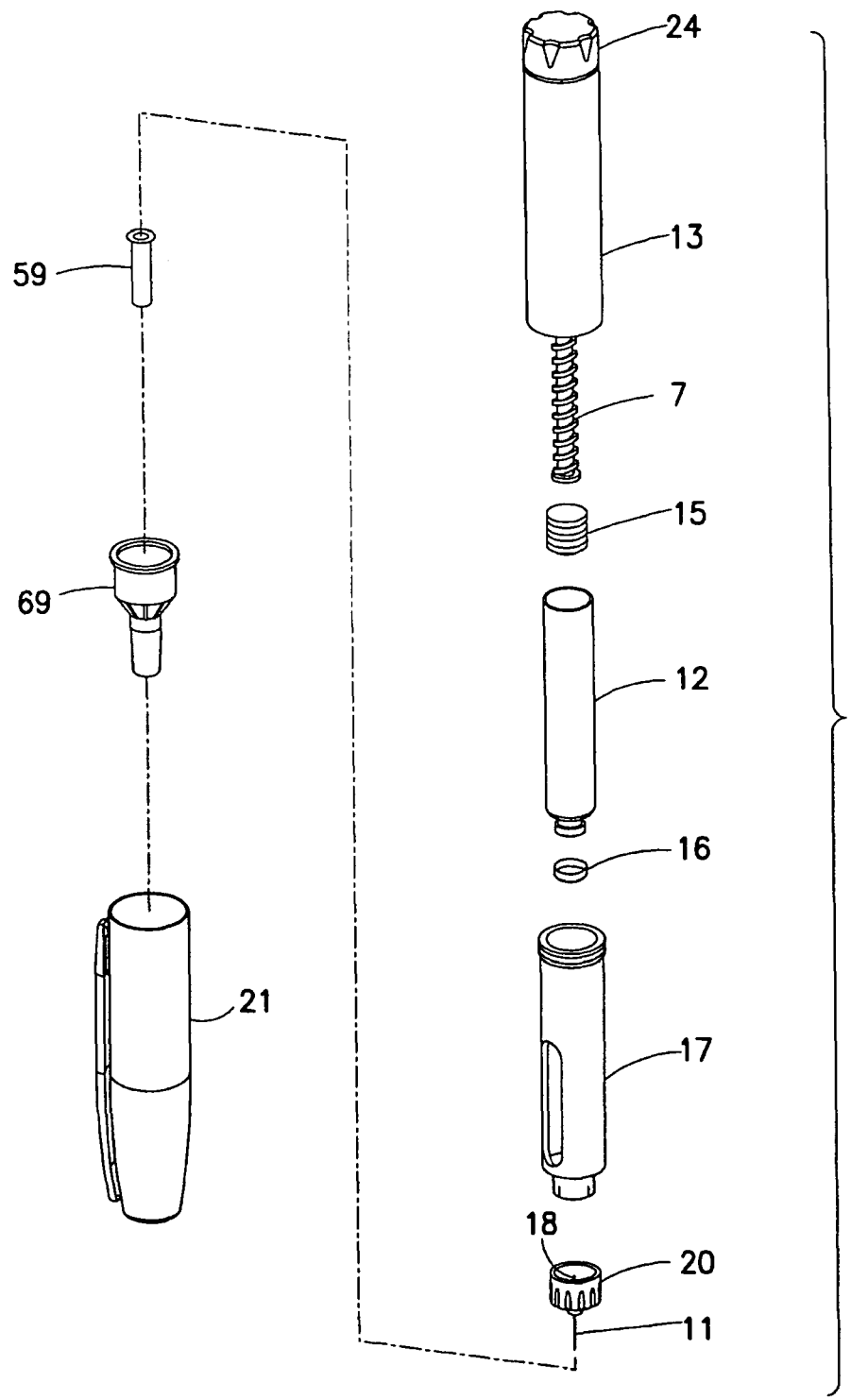
FIG. 3 is an exploded perspective view of the drug delivery pen of FIG. 2.
Figure 4:
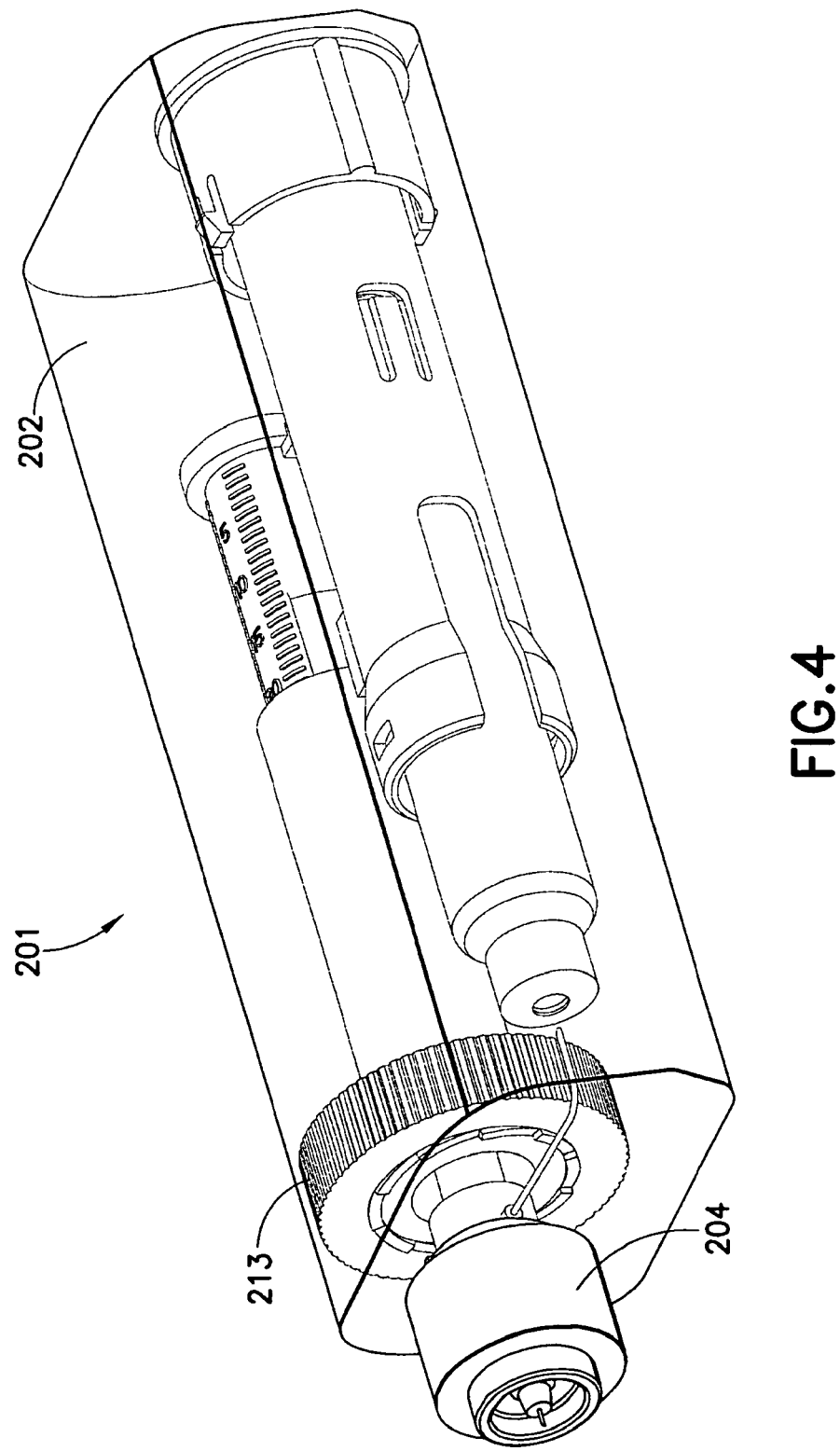
FIG. 4 is a perspective view of a drug delivery device according to a first exemplary embodiment of the present invention.
Figure 5:
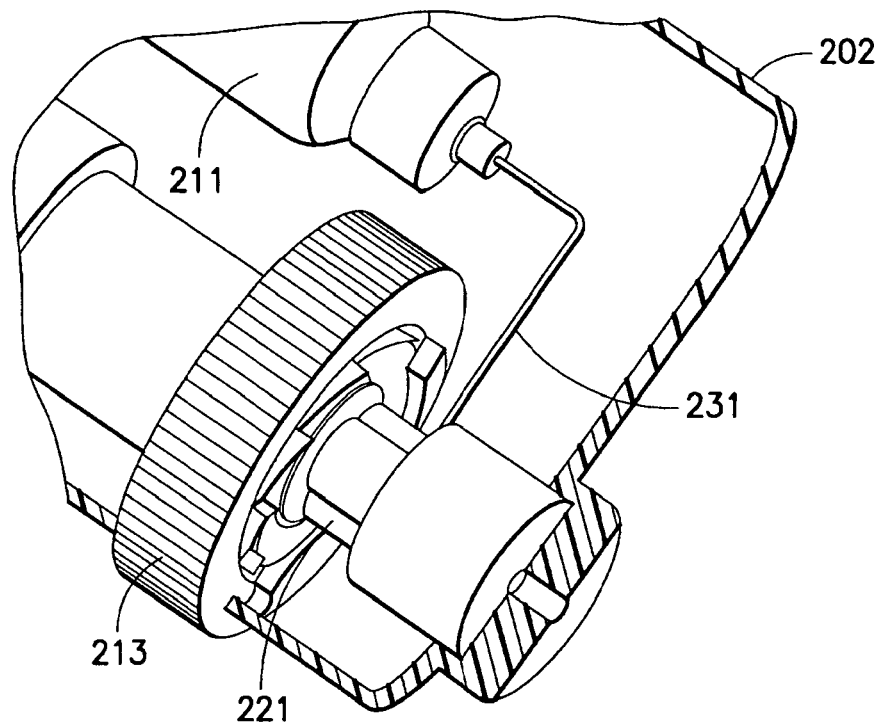
FIG. 5 is a partial perspective view in cross section of the drug delivery device of FIG. 4.
Figure 9:
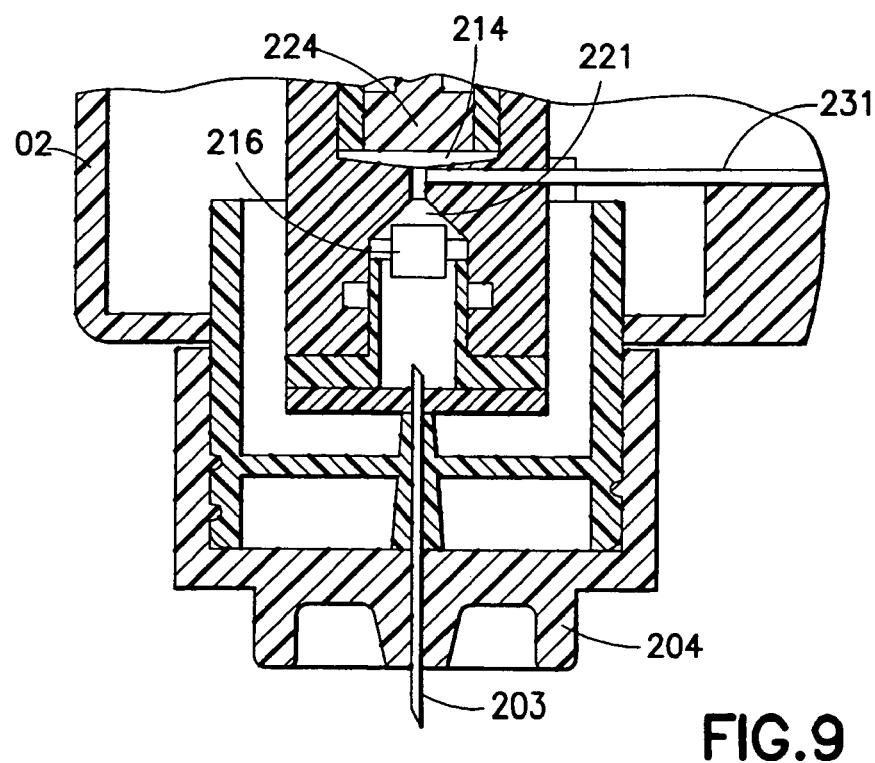
FIG. 9 is a partial front elevational view in cross section of the drug delivery device of FIG. 4.
Figure 8:
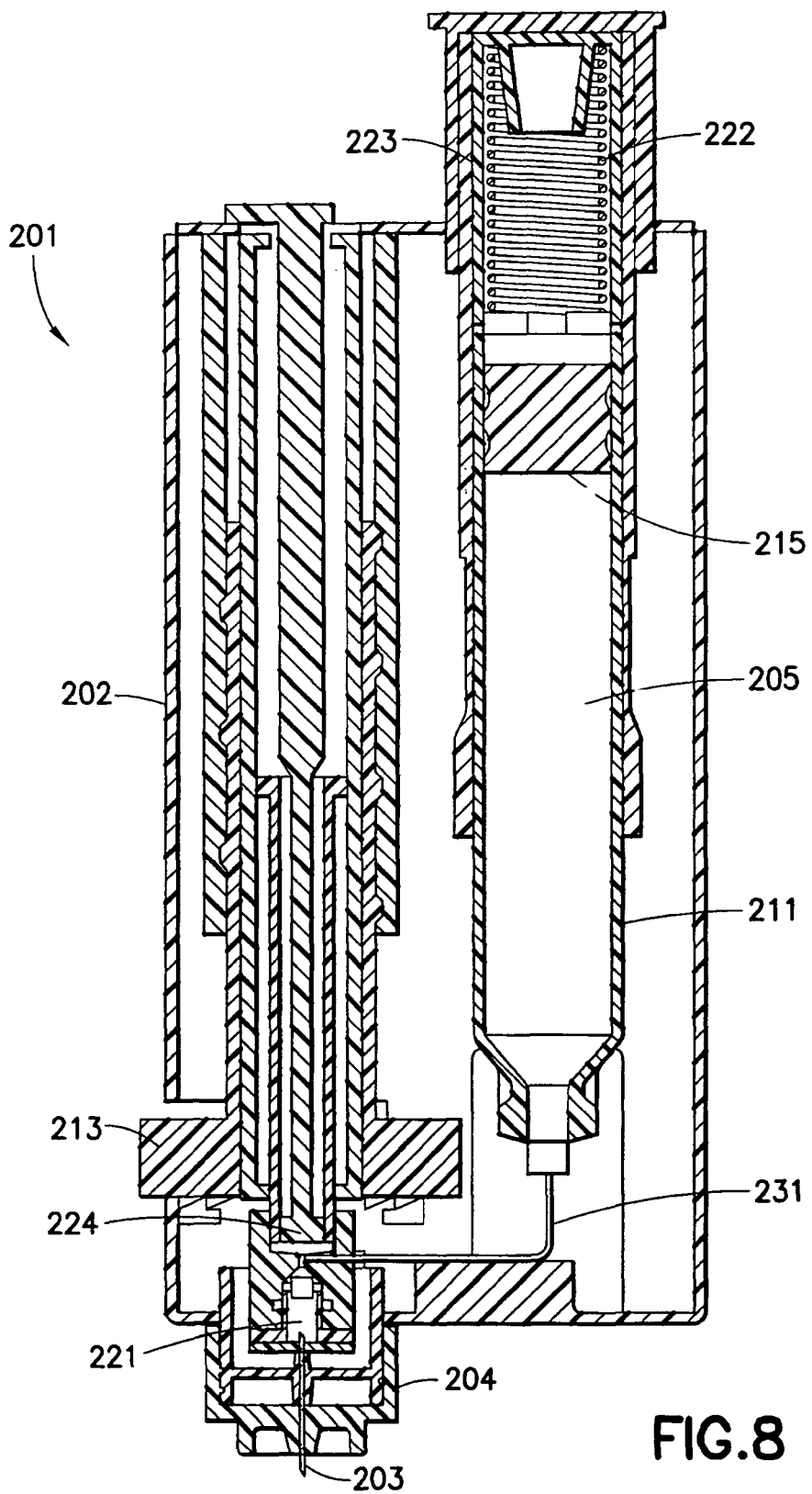
FIG. 8 is a front elevational view in cross section of the drug delivery device of FIG. 4.

Component deformation due to high pressure (or user force) is also limited as the user force is applied directly to the linearly moveable plunger rod 212 of the smaller second chamber 221, thereby eliminating the need for force transfer and amplification mechanisms (from the user input on dose knob 24 to the cartridge stopper 15 of FIG. 3) often used in existing drug delivery pens. In most existing drug delivery pens, the dose delivered is the result of a linear displacement of a drive screw 7 (FIG. 3) that translates a given length dependent on the dialed bolus volume. The dialed bolus determines the stroke length of the injection. The user imparts a force on the dose knob 24 (FIG. 3) and completes the stroke length of the injection. The force and stroke of the injection motion are translated into a torque. The torque is then used to drive the drive screw 7 linearly forward. This type of system can produce inaccuracies at the low end of the dosing range due to the complex relationship between the initial stroke and the final drive screw motion.

After the initial priming mechanism of the cartridge 211 is engaged (a septum-piercing needle piercing a septum of the cartridge 211), the compression spring 222 is released, pressurizing the cartridge 211.

Medicament is moved from the first chamber 205 of the cartridge 211 through the fluid conduit 231 into the second chamber 221 that is equipped with two one-way valves 214 and 216. The filling of the second chamber 221 is accomplished by exerting a force $F_{cs}$ on the original container 211 using a compression spring 222 that creates a pressure greater than the opening pressure of the first valve, $V_1$, 214 but less than the opening pressure of the second external valve, $V_2$, 216. During the injection, the user depresses the plunger rod 212 and the pressure inside the second chamber 221 rises until the pressure exceeds the cracking pressure of the second valve, $V_2$, 216 (and opens the second valve 216) and back-pressure from the intradermal space, at which state the medicament dose is delivered.

The second chamber 221 has a smaller cross sectional area than the first chamber 205 of the cartridge 211, thereby providing higher pressure using the same user input force. Standard 3.0 mL insulin cartridges have a diameter of approximately 9.7 mm, thereby resulting in a cross sectional area of $A=\pi r^2=4.85^2*3.14159=73.9$ mm². In a preferred embodiment of the drug delivery device 201, the second chamber 221 of the drug delivery device 201 has a diameter of 3.5 mm resulting in a cross sectional area of $1.75^2*3.14159=9.62$ mm². For a given pressure, P, a force multiplication is achieved using the following relationships: $P=F_1/A_1$, $P=F_2/A_2$. Therefore, $F_1/A_1=F_2/A_2$. The force multiplier $M_f$, $F_1/F_2$, becomes the ratio of the areas, $A_1/A_2$, $M_f=73.9/9.62=7.7$.

Therefore, the drug delivery device 201 according to an exemplary embodiment of the present invention requires approximately seven (7) times less force to achieve the same injection pressure as a device that applies force directly to the insulin cartridge 12 (FIG. 3) without force amplification.

Figure 12:
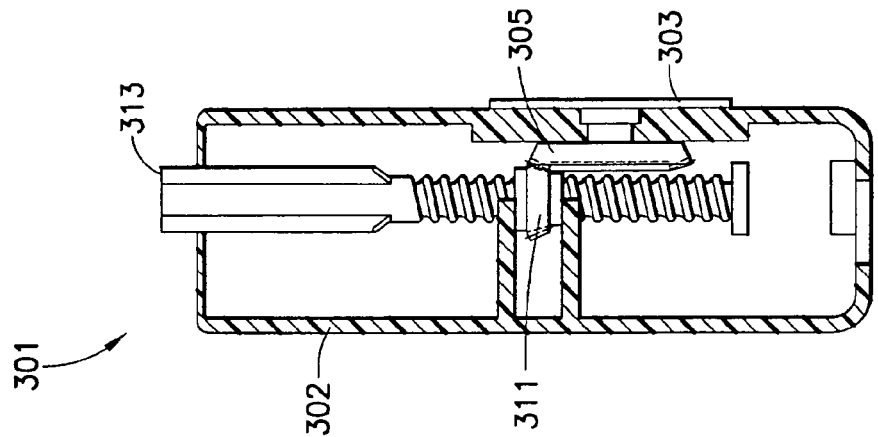
FIG. 12 is a side elevational view in cross section of the drug delivery device of FIG. 10.
Figure 11:
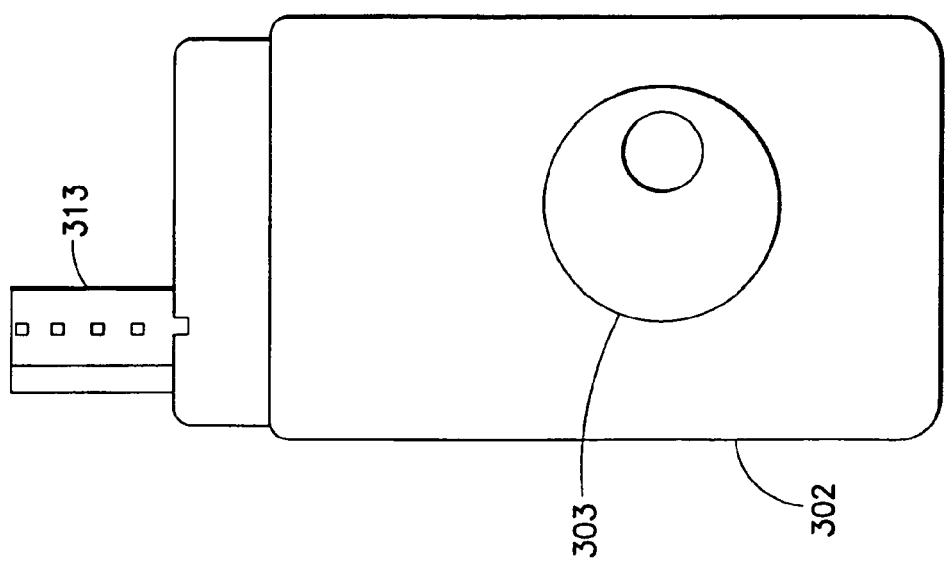
FIG. 11 is a front elevational view of the drug delivery device of FIG. 10.
Figure 13A:
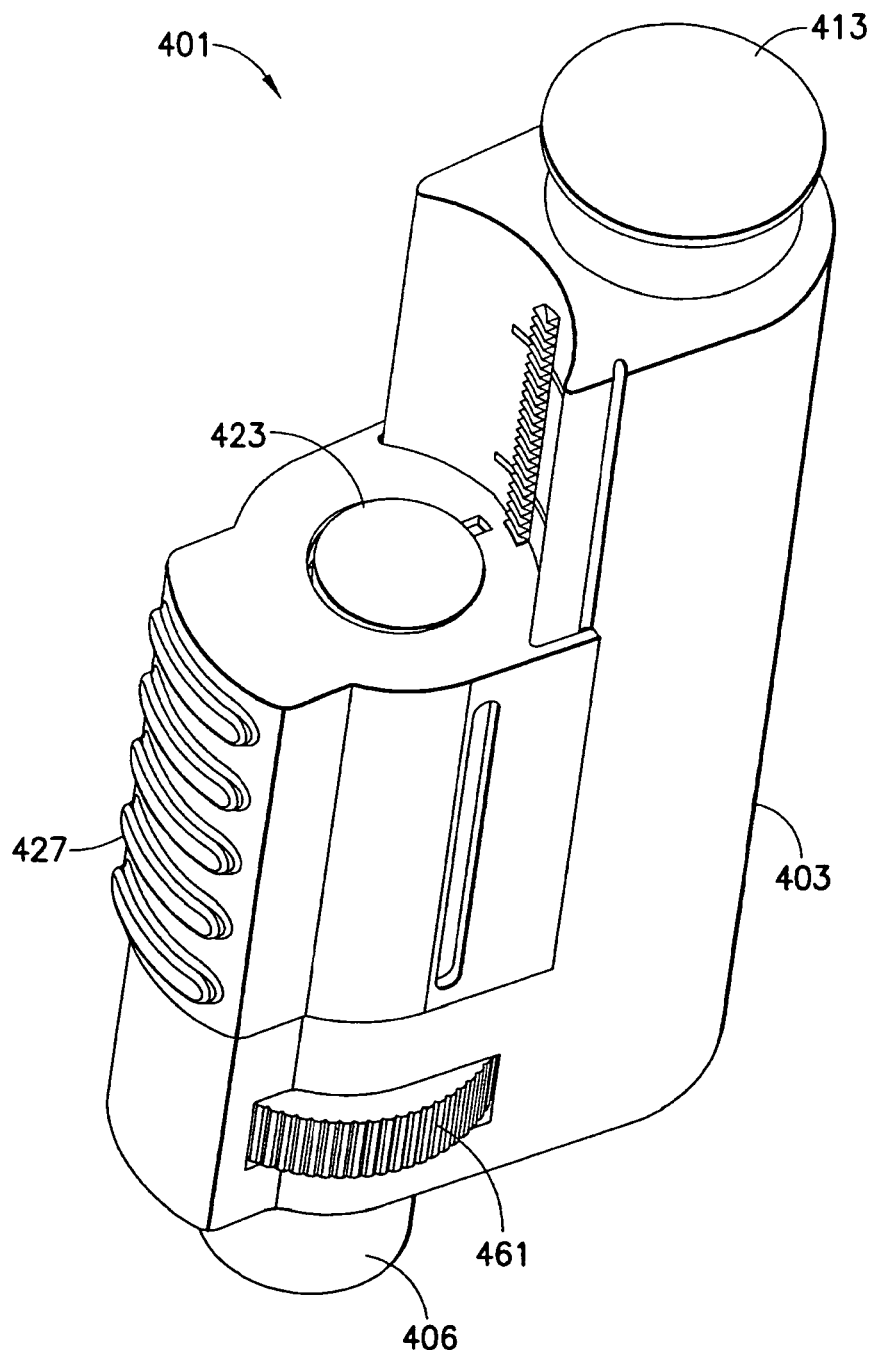
FIGS. 13A, 13B and 13C are perspective views of a drug delivery device according to a third exemplary embodiment of the present invention.
Figure 13B:
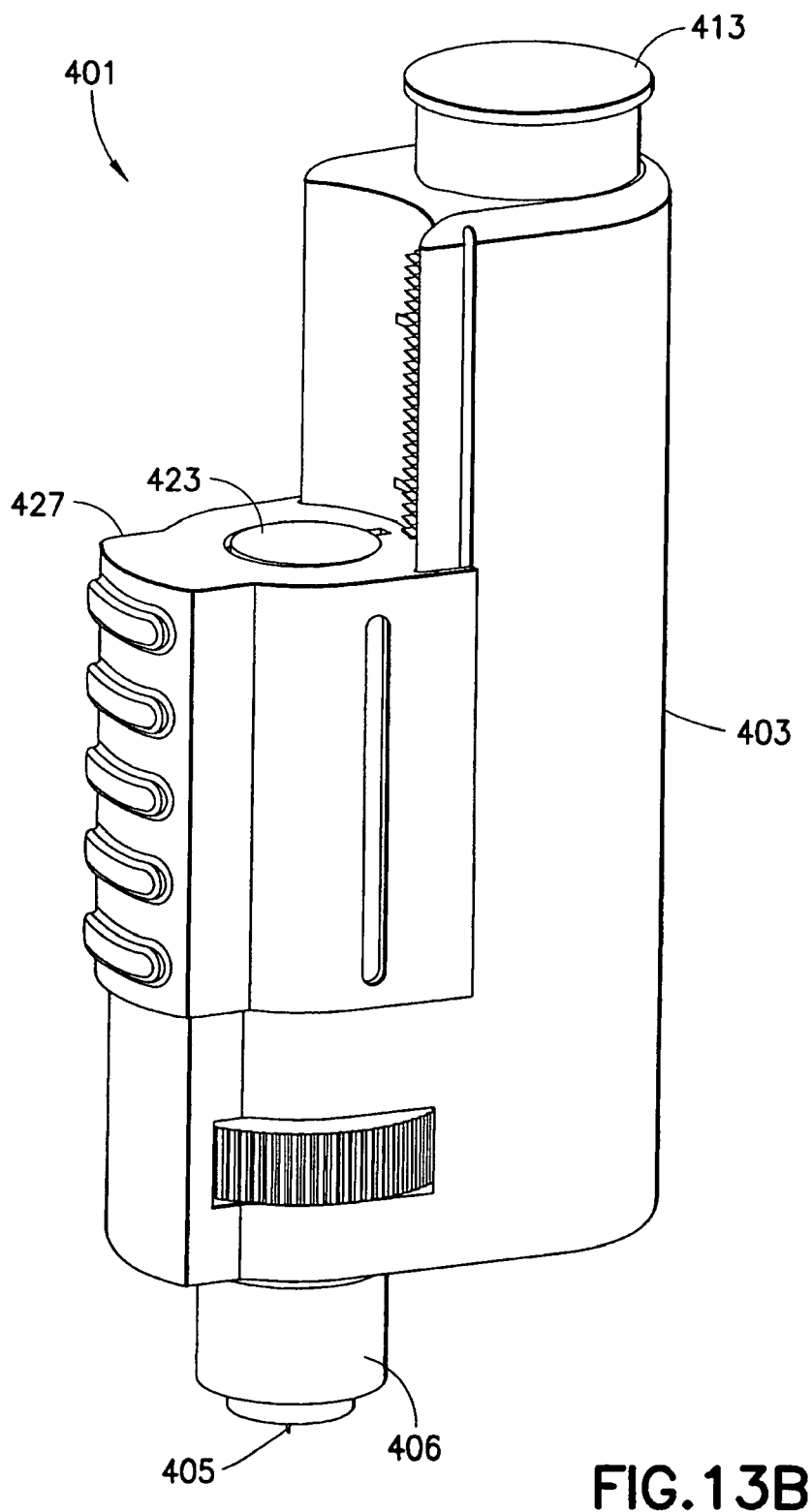
Figure 13C:
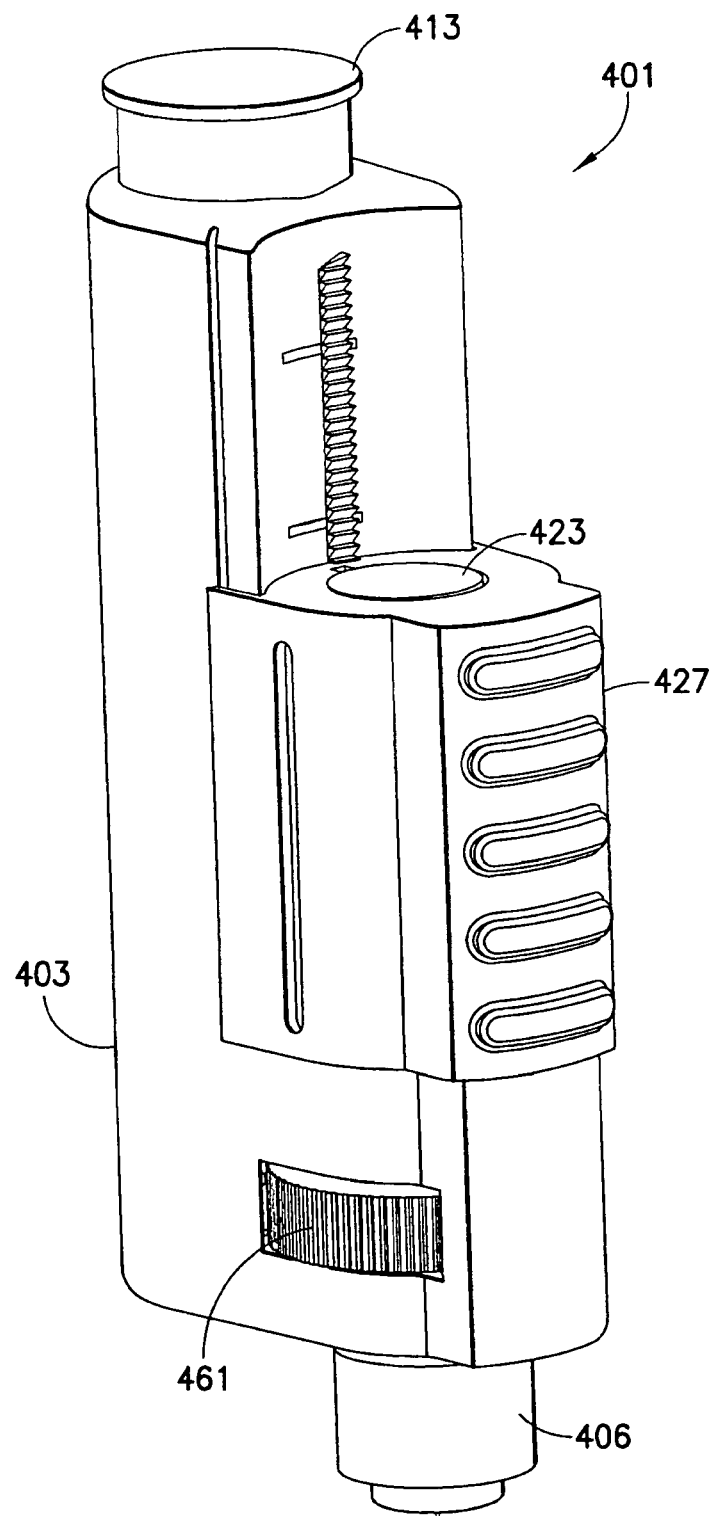
Figure 14A:
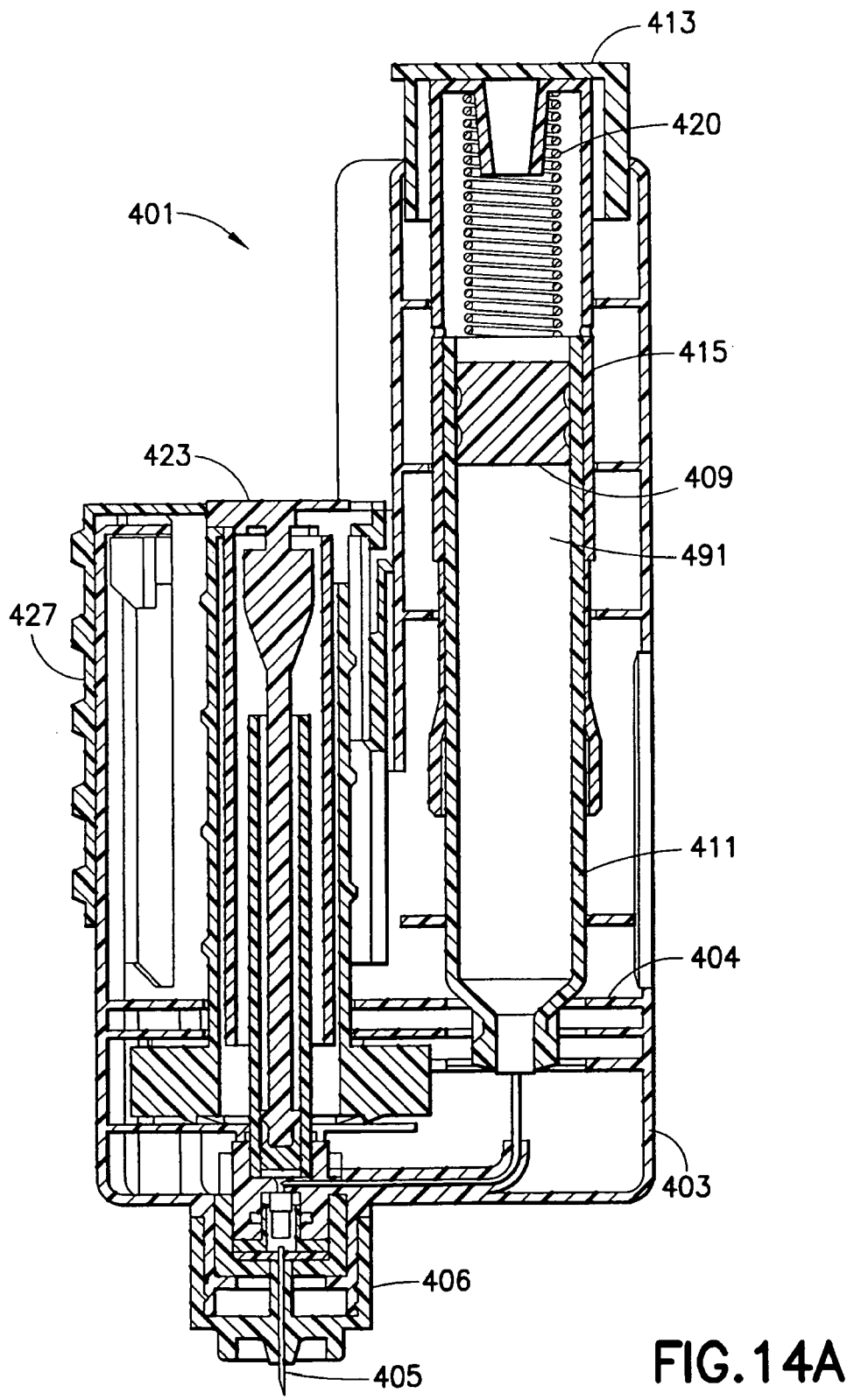
FIGS. 14-26 illustrate priming and pressurization of the cartridge of the drug delivery device of FIG. 13.
Figure 14B:
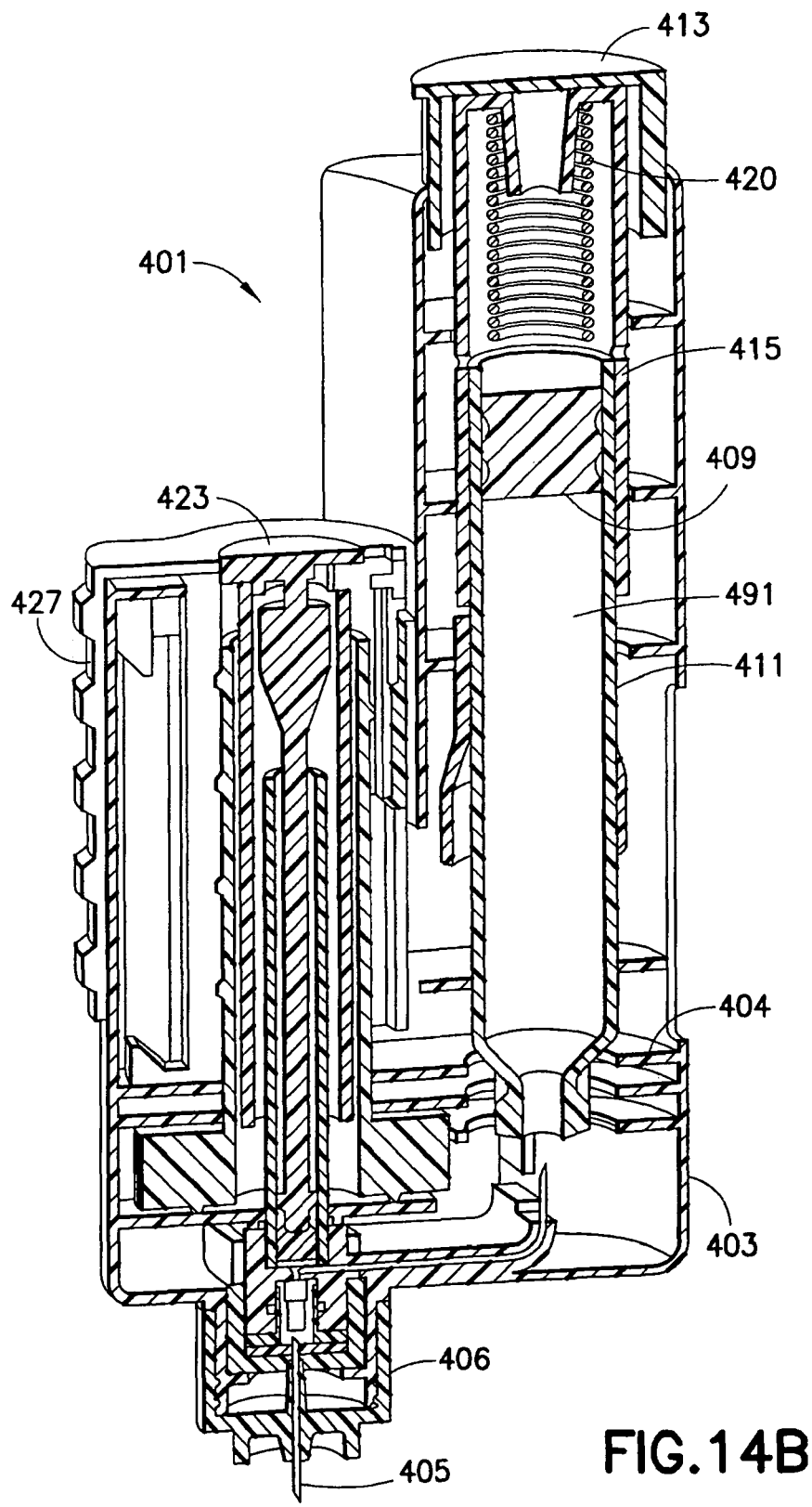
Figure 14C:
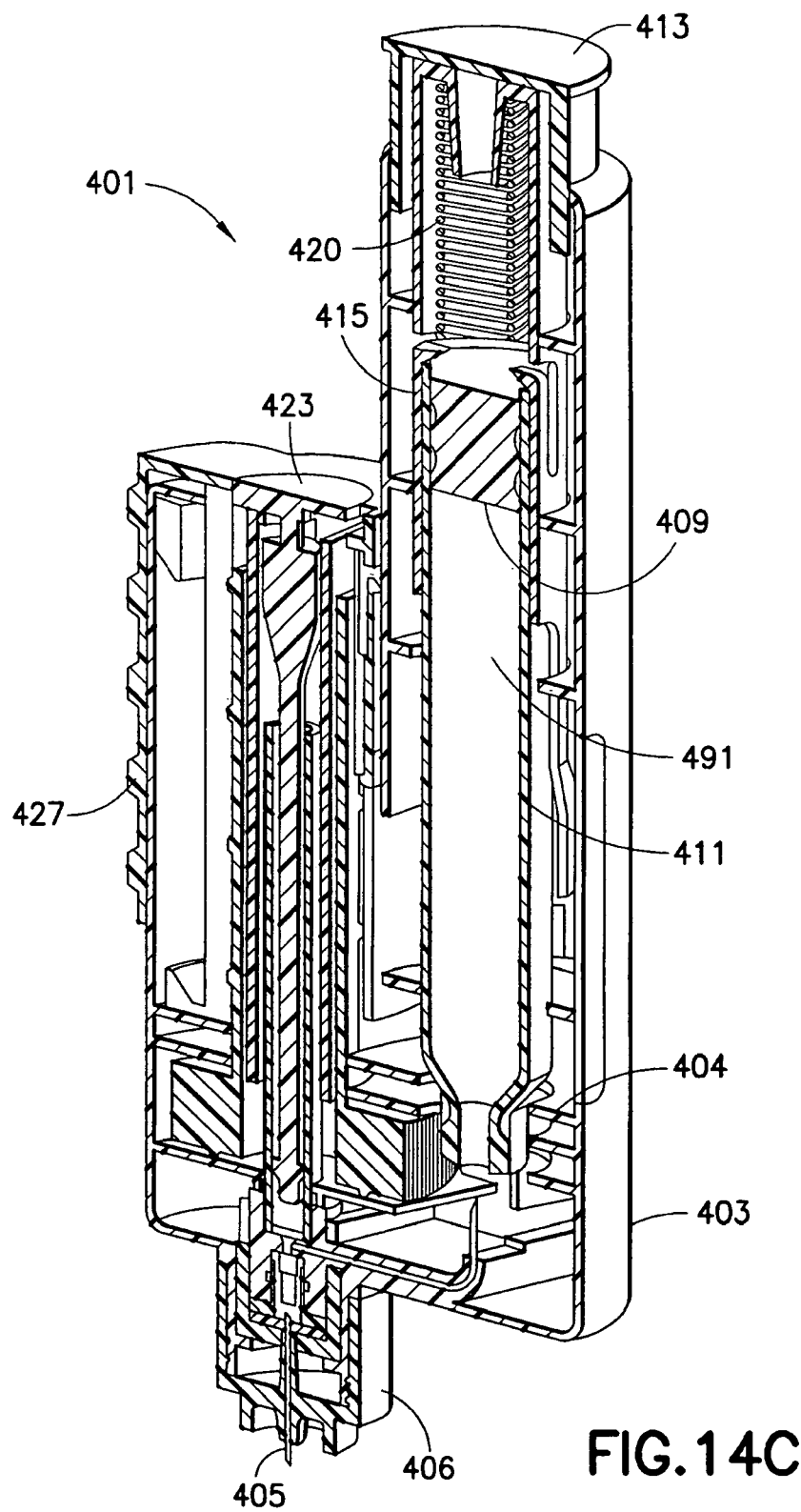

Alternatively, as shown in FIGS. 10-12, the user dials a medicament dose by turning a dose setting wheel 303 of a drug delivery device 301 according to a second exemplary embodiment of the present invention. As shown in FIG. 11, a longitudinal axis through a center of the dose setting wheel 303 is substantially perpendicular to a direction of the travel of a plunger rod 313 driven by the dose setting wheel 303. Otherwise, the functionality and underlying technical principles of the drug delivery device 301 are substantially similar to those of the first exemplary embodiment shown in FIGS. 4-9.

As shown in FIG. 12, a dose setting wheel gear 305 is rotatably engaged with a plunger rod gear 311. The dose setting wheel gear 305 is rotated by the dose setting wheel 303, which rotates the plunger rod gear 311. The plunger rod gear 311 is fixed to the device housing 302 and is rotatably disposed on the plunger rod 313. Accordingly, rotation of the plunger rod gear 311 causes the plunger rod 313 to move linearly through the fixed plunger rod gear 311. Rotation of the dose setting wheel 305 when setting a medicament dose results in upward travel of the plunger rod 313, as shown in FIG. 11. The plunger rod 313 is then pushed back into the device housing 302 to inject a medicament dose from the second chamber and into a patient's skin at an injection site.

Another exemplary embodiment of a drug delivery device 401 of the present invention is shown in FIGS. 13-49. The drug delivery device 401 operates similarly to the drug delivery device 201 according to the first exemplary embodiment shown in FIGS. 4-9. A medicament dose is set, the second chamber is filled, and the medicament dose is delivered intradermally. The drug delivery device 401 allows priming and pressurization of the cartridge, employs valves to activate filling of the second chamber and dose delivery, and allows a medicament dose to be set.

Figure 15:
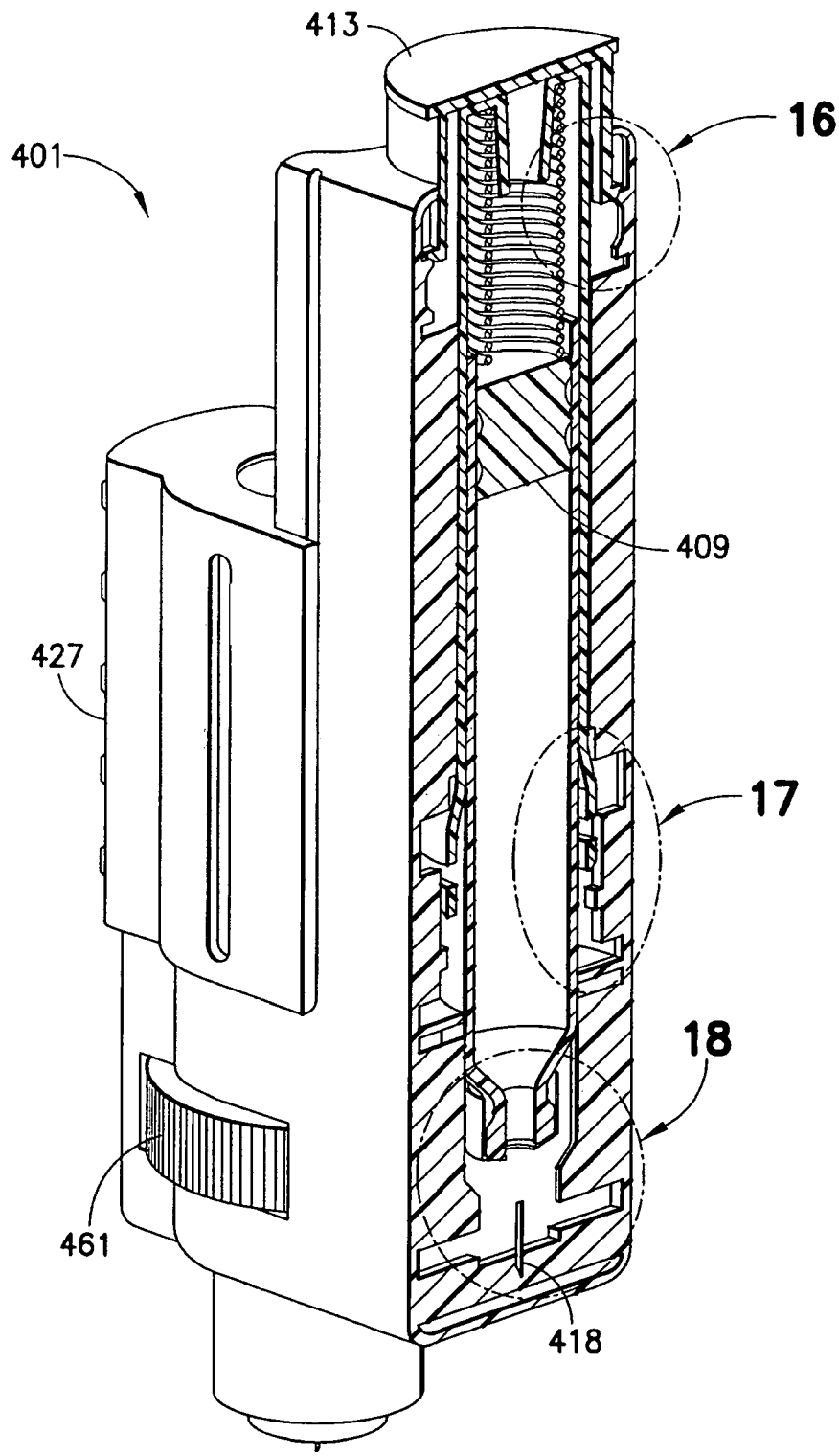
Figure 17:
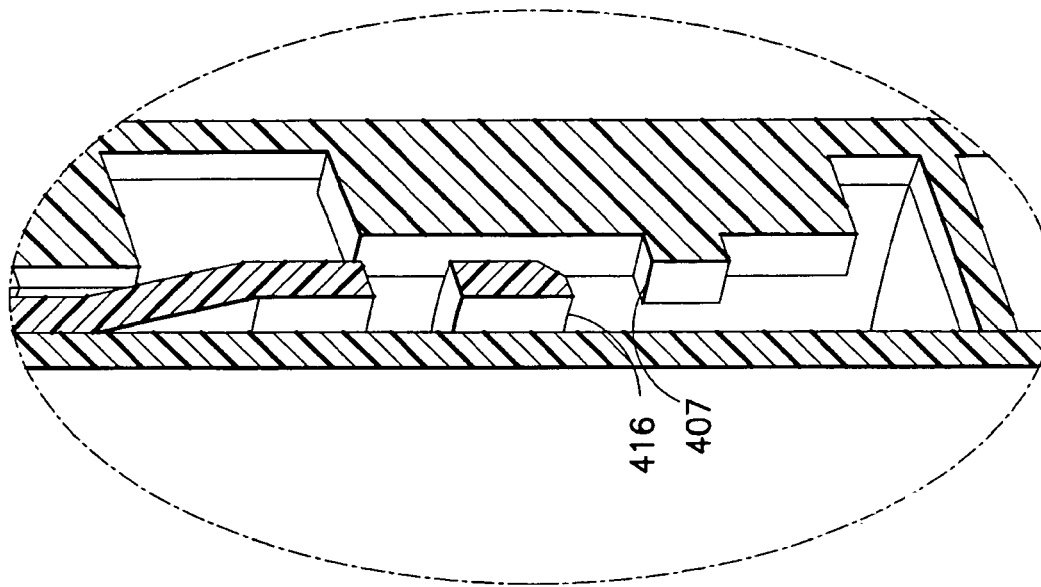
Figure 16:
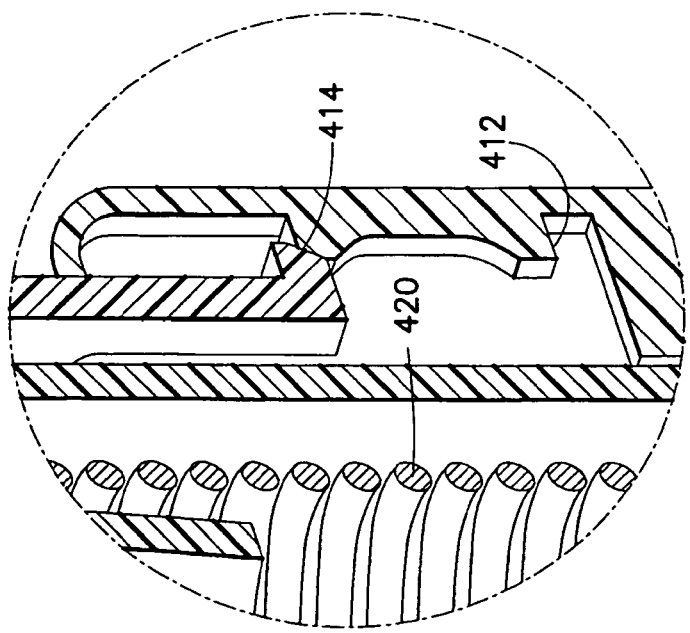

FIGS. 14-26 illustrate the operation of cartridge priming and pressurization. FIGS. 16-20 show the drug delivery device 401 in a shipping state. The cartridge 411 is pressurized and connected to the injection path upon first use. Prior to the first use, the cartridge 411 is in a first position such that a cartridge septum 408 is spaced from a septum-piercing needle 418, as shown in FIGS. 15 and 19. A button snap 414 of the cartridge button 413 is spaced from a first protrusion 412 of the device housing, as shown in FIGS. 15 and 16. A snap 416 of a cartridge housing 415 is spaced from a second protrusion 407 of the cartridge housing 415, as shown in FIGS. 15 and 17. Teeth 410 of the cartridge housing 415 engage a compression spring 420 to space the compression spring 420 from a stopper 409 disposed in the cartridge 411.

Figure 18:
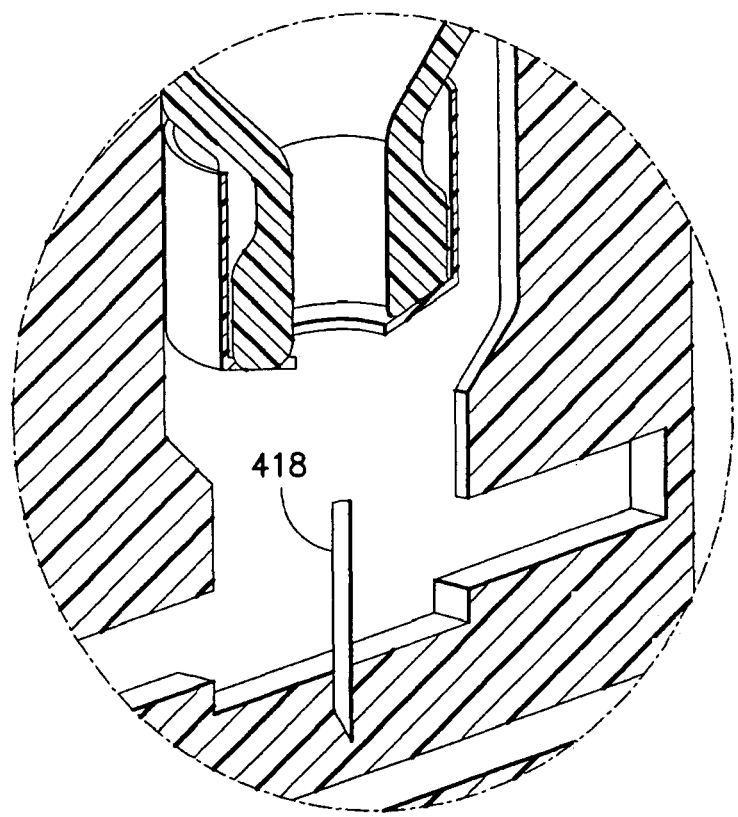
Figure 20:
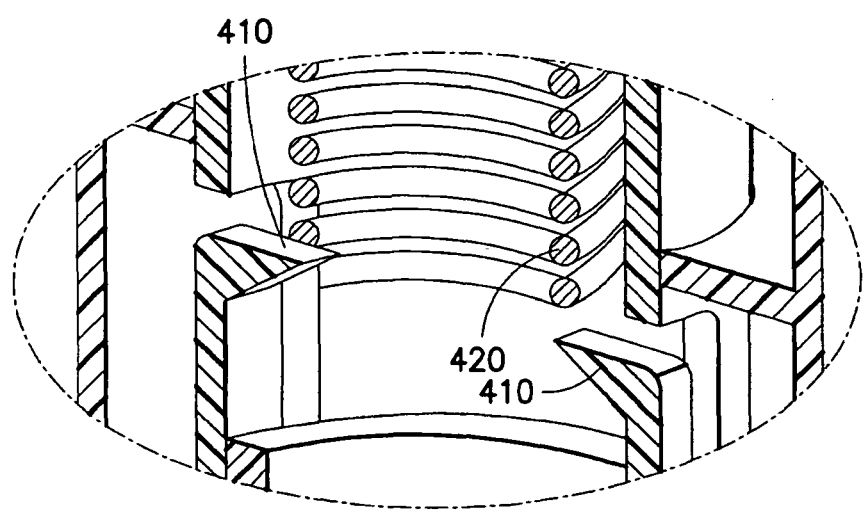
Figure 19:
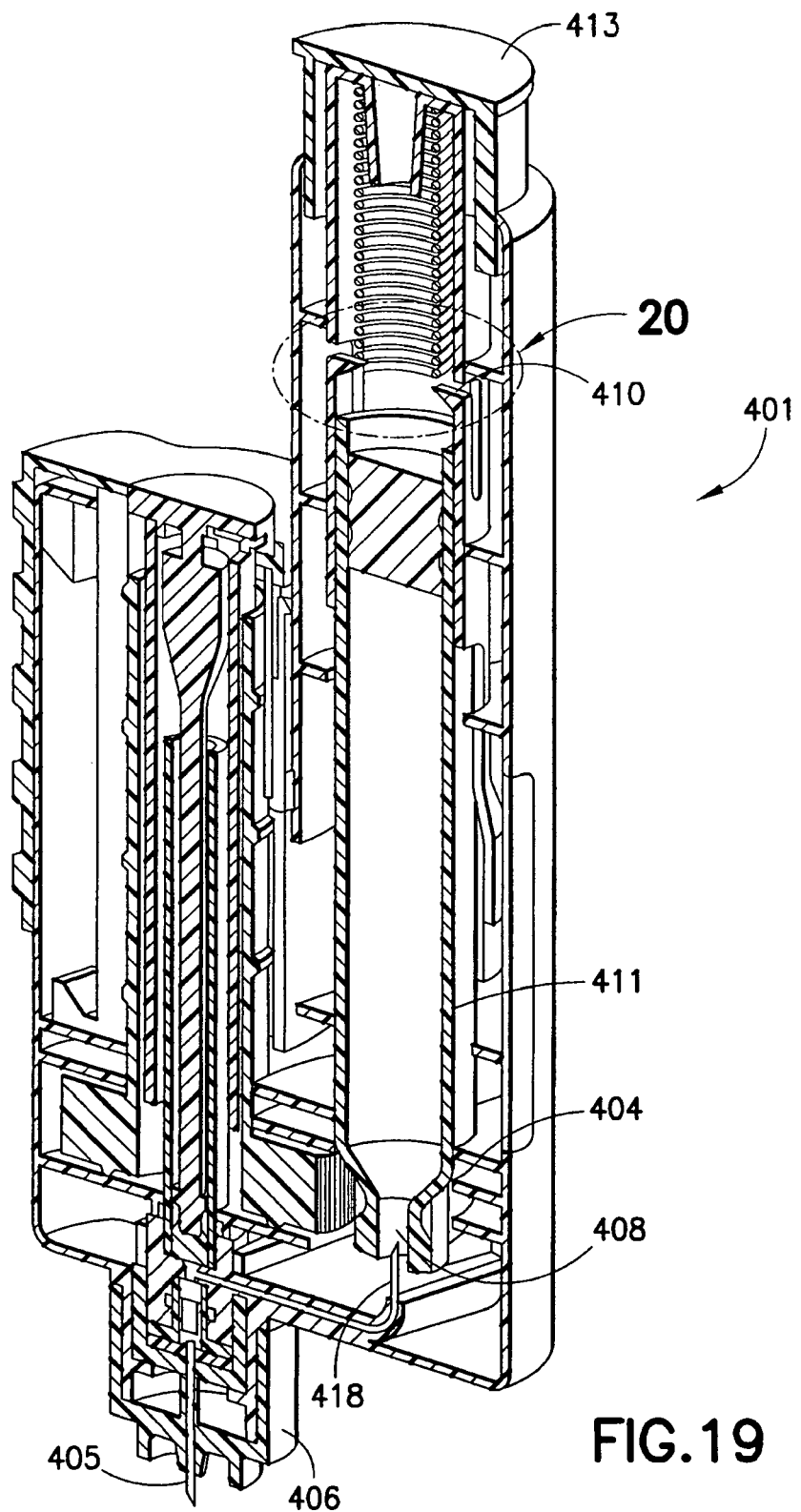
Figure 21:
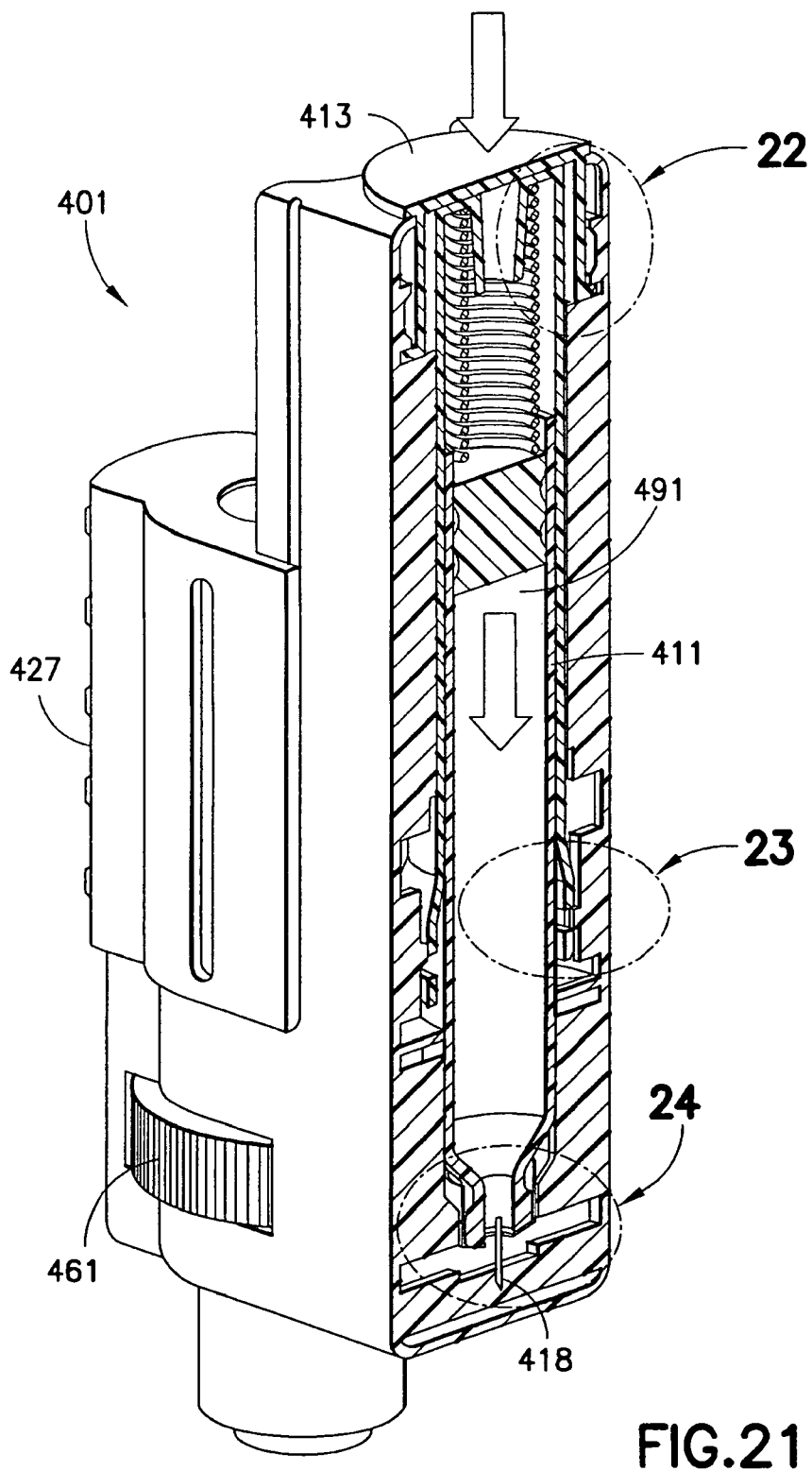
Figure 22:
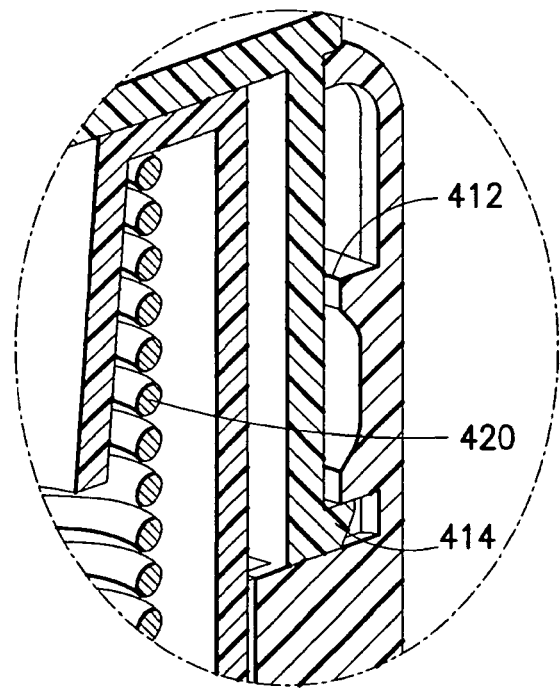
Figure 23:
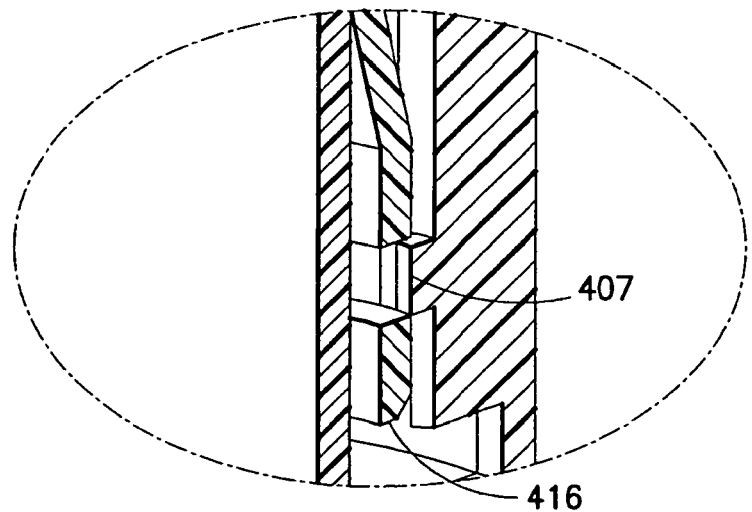
Figure 24:
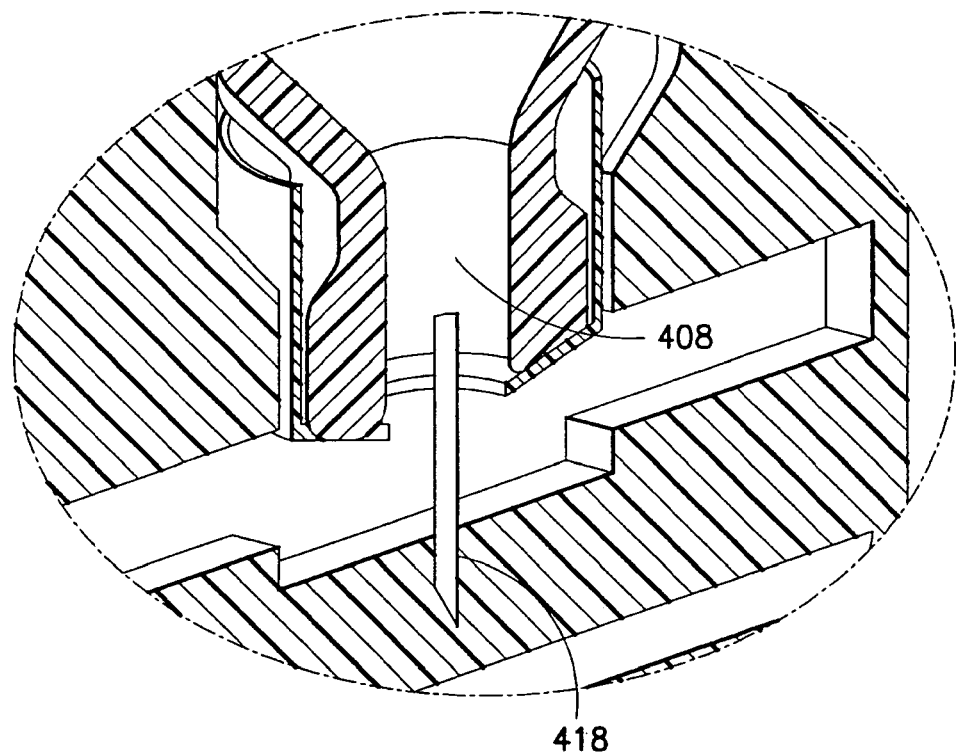
Figure 26:
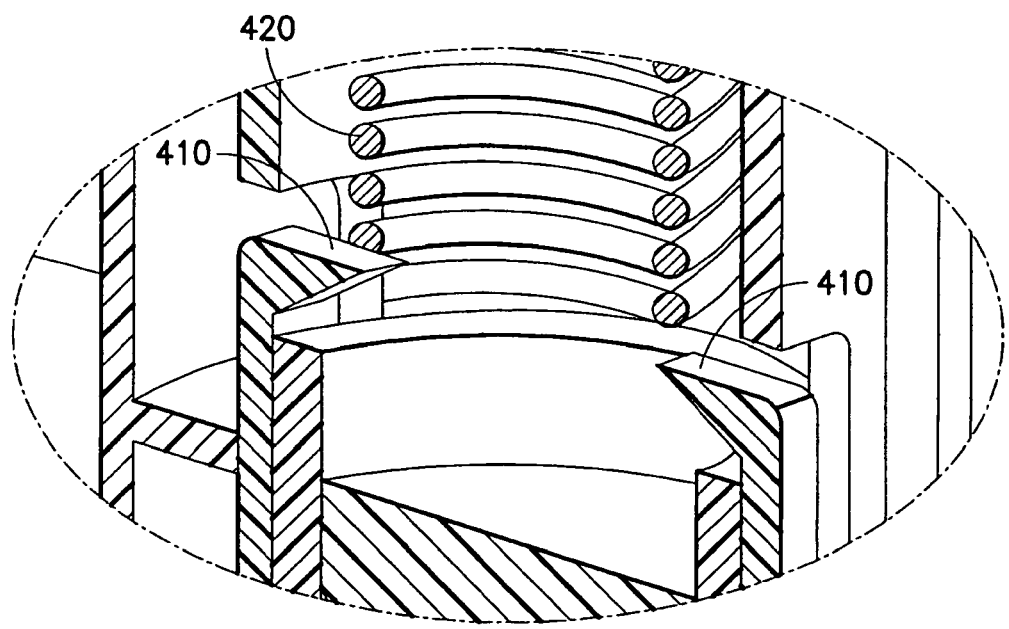
Figure 25:
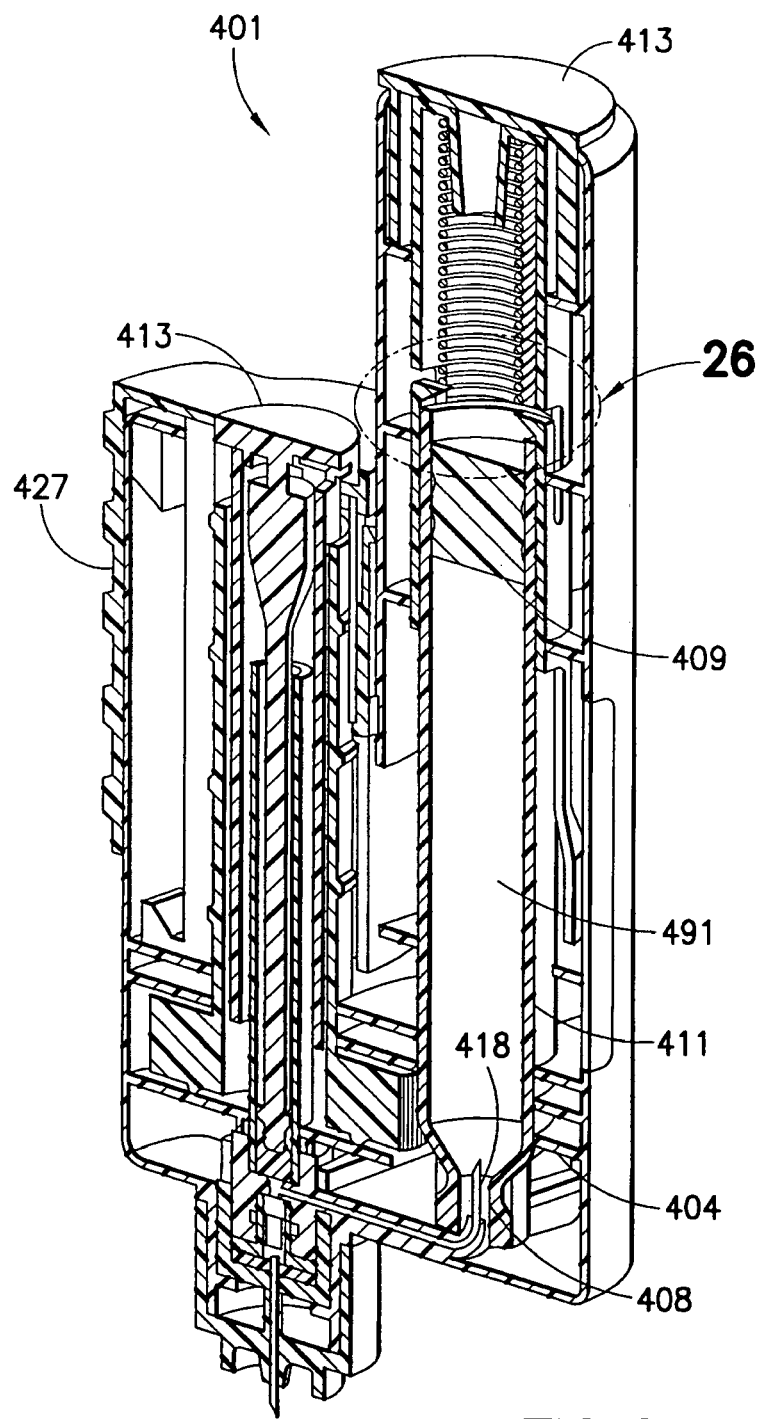

To prime and pressurize the cartridge 411, the cartridge 411 is moved from the first position shown in FIGS. 15-20 to a second position shown in FIGS. 21-26 in which the septum-piercing needle 418 pierces the cartridge septum 408. FIGS. 21-26 show the drug delivery device 401 when the cartridge button 413 is depressed. The user pushes the cartridge button 413 downwardly into the device housing 403 to prime and pressurize the cartridge 411. The cartridge button 413 is locked into the device housing 403, as shown in FIGS. 21 and 22, when the button snap 414 passes over the first protrusion 412. The snaps 416 of the cartridge housing 415 lock the cartridge housing 415 into the device housing 403, as shown in FIGS. 21 and 23, by passing over the second protrusion 410. The septum-piercing needle 418 pierces the septum 408 of the cartridge 411, which is positioned by device housing ribs 404, as shown in FIGS. 18 and 24. The cartridge housing 415 has teeth 410 that are flexed radially outwardly, as shown in FIG. 26, as the cartridge button 413 engages the cartridge housing 415 and pushes the cartridge housing 415 downwardly, thereby flexing the teeth 410 outwardly. The compression spring 420 then passes through the teeth 410 of the cartridge housing 415 and engages the stopper 409 of the cartridge 411.

Figure 27:
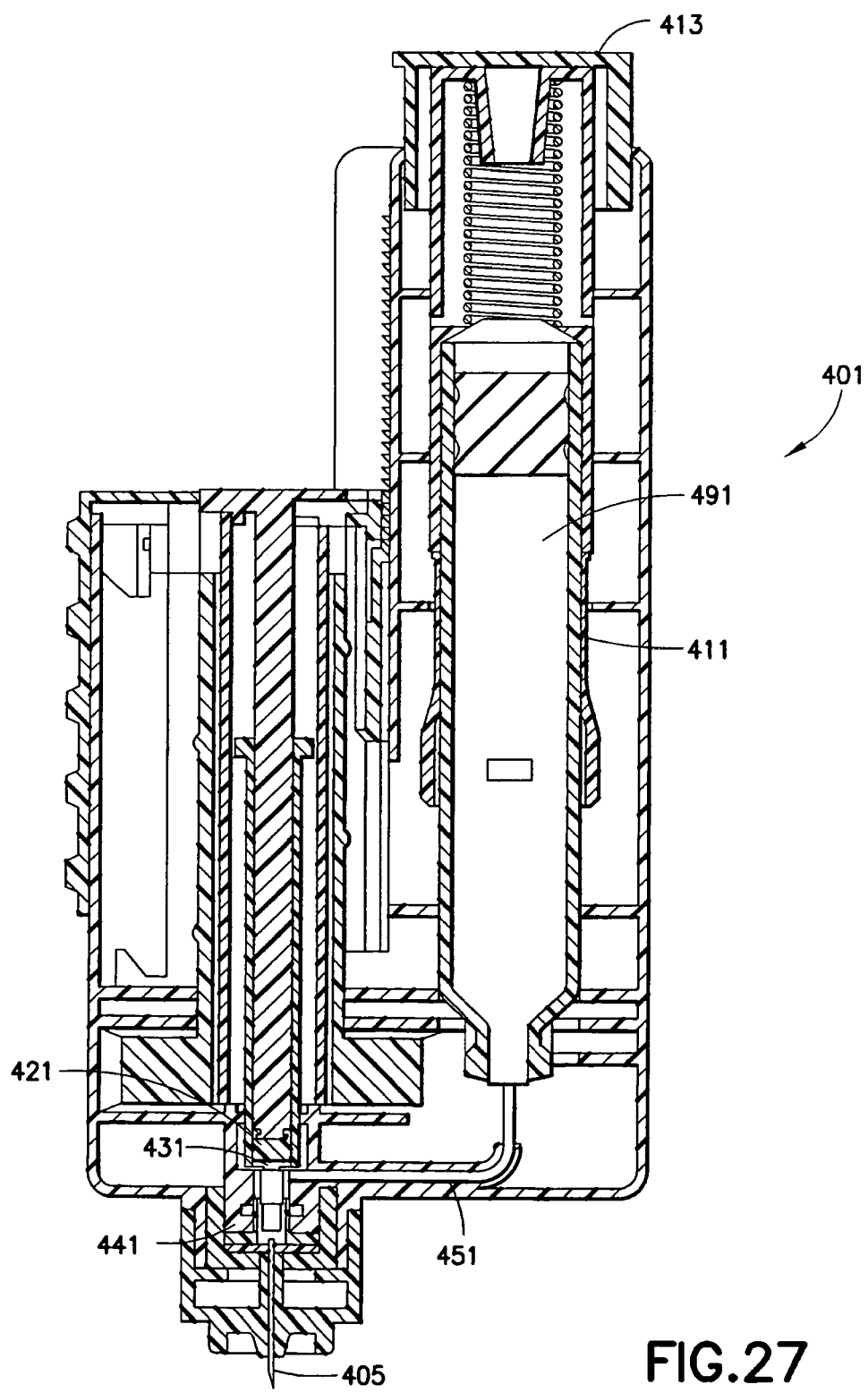
FIG. 27 illustrates a two-valve system used in the drug delivery device of FIG. 13.
Figure 35:
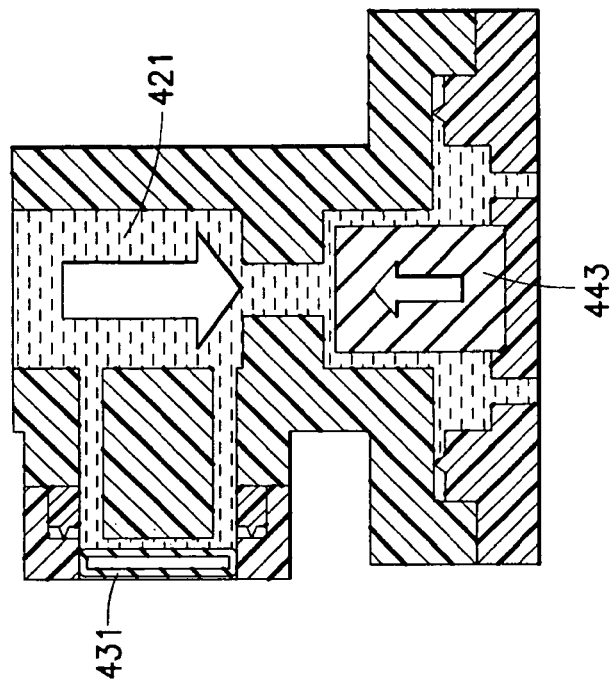
FIGS. 34 and 35 illustrate operation of a pressure relief valve as the second valve assembly of the drug delivery device of FIG. 13.
Figure 34:
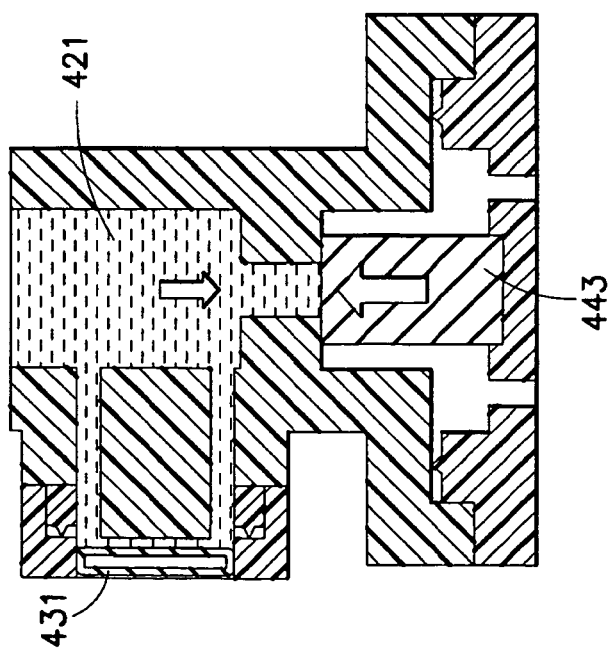

FIG. 27 illustrates the two-valve system used in the drug delivery device 401. A first valve 431 regulates flow between the first chamber 491 of the cartridge 411 and the second chamber 421. Any suitable valve may be used, such as a disk valve (FIGS. 28 and 29) or a flap valve (FIGS. 30-33). The first valve 431 allows flow from the first chamber 491 of the cartridge 411 to the second chamber 421 when the second chamber is being filled. The first valve 431 blocks flow from the second chamber 421 to the first chamber 491 of the cartridge 411 when injecting a medicament dose. A second valve 441 regulates flow from the second chamber 421 to the delivery needle 405. Any suitable valve may be used, such as a relief valve (FIGS. 34 and 35). The second valve 441 opens when injecting pressure is applied to the second chamber 421.

Figure 28:
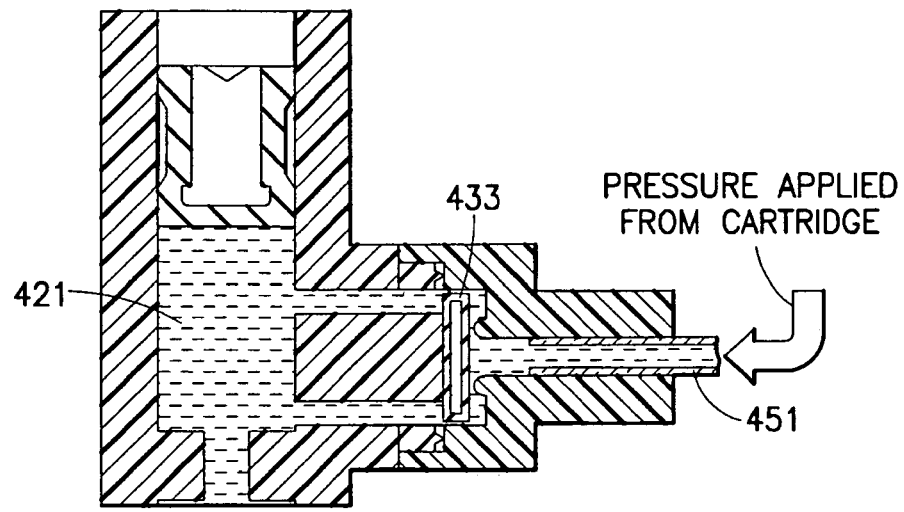
FIGS. 28 and 29 illustrate operation of a disk valve as the first valve assembly of the drug delivery device of FIG. 13.
Figure 29:
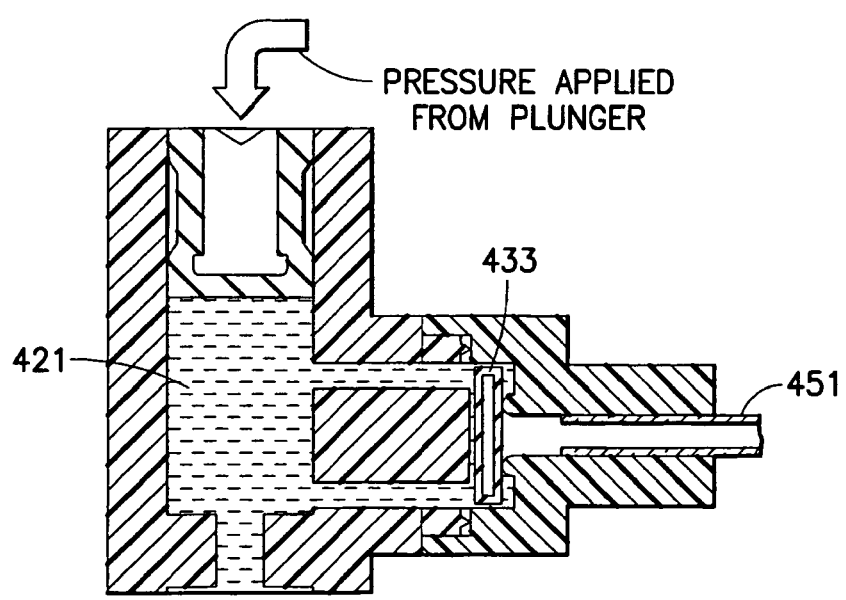

A disk valve 433 is shown in FIGS. 28 and 29. When pressure is applied from the first chamber 491 of the cartridge 411, as shown in FIG. 28, the disk valve 433 is spaced away from the conduit 451 such that medicament may flow into the second chamber 421 from the first chamber 491. When pressure is applied from the plunger 423, as shown in FIG. 29, the disk valve 433 is moved to a position abutting the fluid conduit 451 such that medicament is prevented from entering the fluid conduit 451 and flowing back to the first chamber 491 of the cartridge 411. The disk valve seats against the surface opposite the higher pressure.

Figure 30:
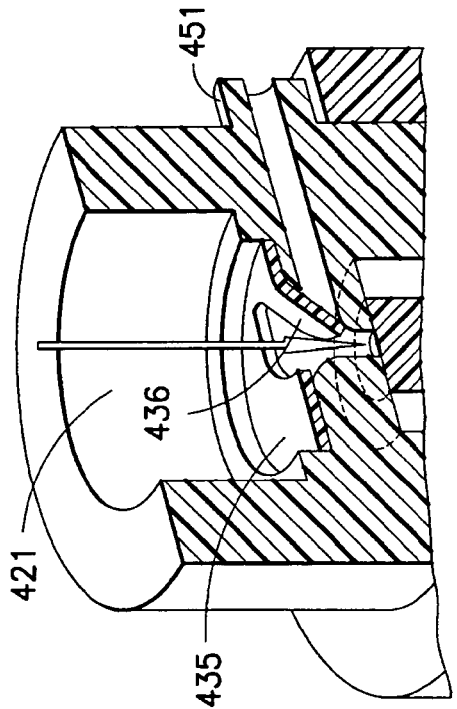
FIGS. 30-33 illustrate operation of a flap valve as the first valve assembly of the drug delivery device of FIG. 13.
Figure 32:
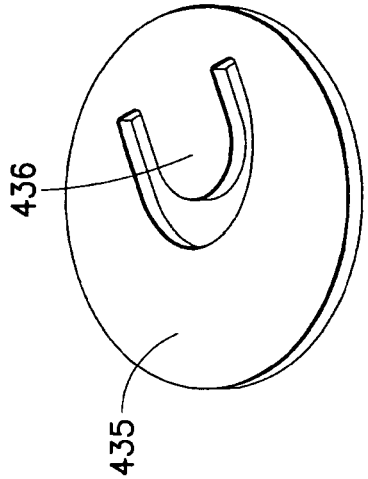
Figure 31:
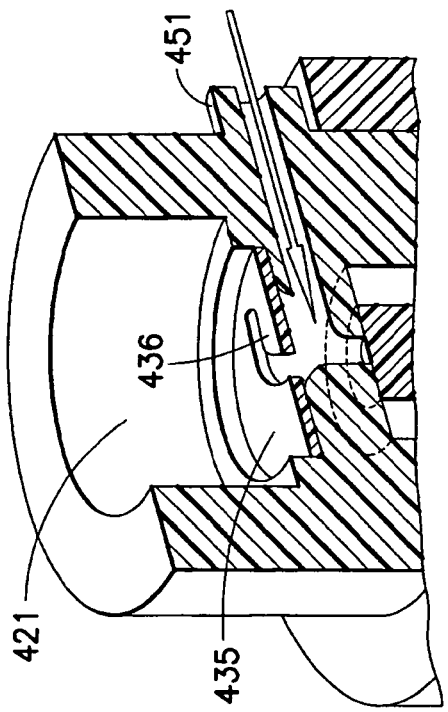
Figure 33:
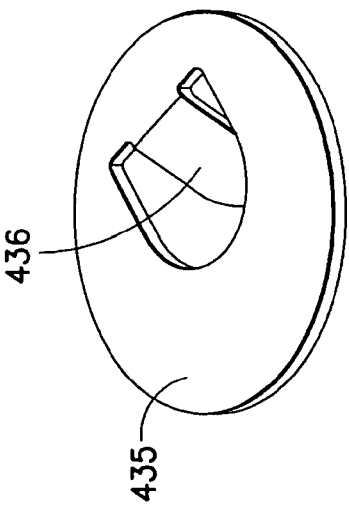

A flap valve 435 is shown in FIGS. 30-33. When pressure is applied from the cartridge 411, as shown in FIG. 30, the flap 436 of the flap valve 435 is disposed substantially horizontally (FIG. 33) such that medicament may flow into the second chamber 421. When pressure is applied from the plunger, as shown in FIG. 31, the flap 436 of the flap valve 435 is moved downwardly (FIG. 32) such that medicament is prevented from entering the fluid conduit 451 and flowing back to the first chamber 491 of the cartridge 411.

FIGS. 34 and 35 illustrate operation of a pressure relief valve 443 when used as the second valve. As shown in FIG. 34, the pressure relief valve 443 is in a first position that prevents medicament from exiting the second chamber 421 when the pressure in the second chamber 421 is less than the pre-load pressure of the pressure relief valve (such as a rubber stopper). When the pressure in the second chamber 421 exceeds the pre-load pressure of the pressure relief valve 443, as shown in FIG. 35, the pressure relief valve moves downwardly to a second and open position to allow medicament to exit the second chamber 421. The first valve 431 prevents medicament from entering the fluid conduit 451 and flowing back to the first chamber 491 of the cartridge.

Figure 36:
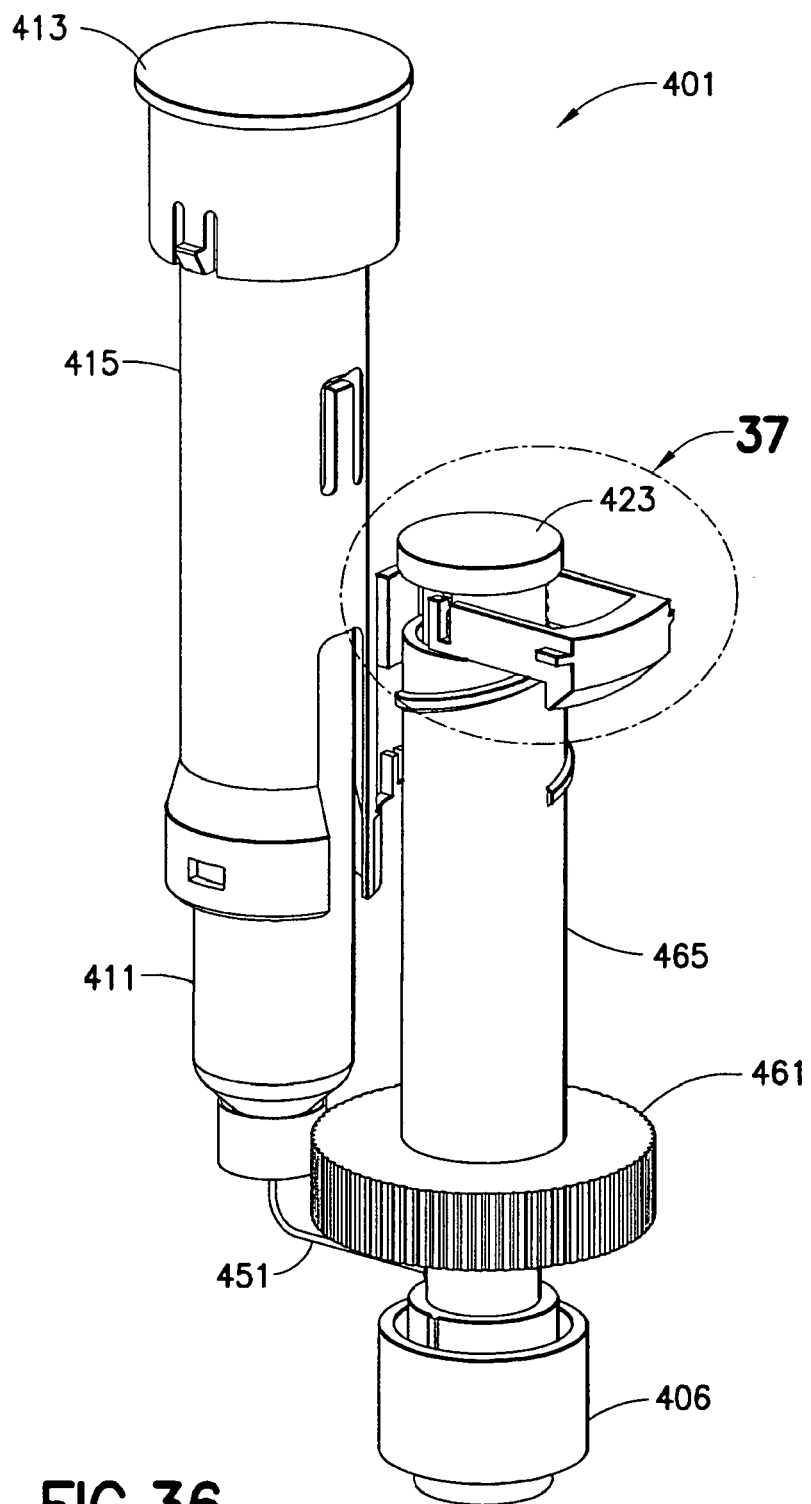
FIGS. 36-39 illustrate operation of the filling of a second chamber of the drug delivery device of FIG. 13.
Figure 37:
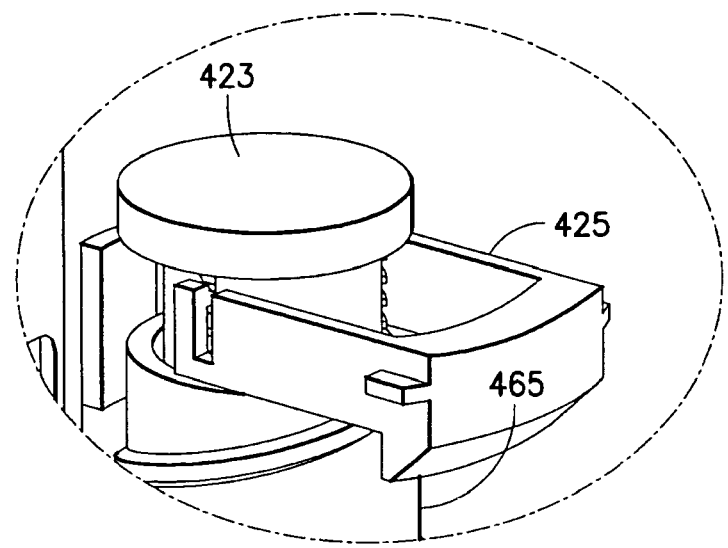
Figure 39:
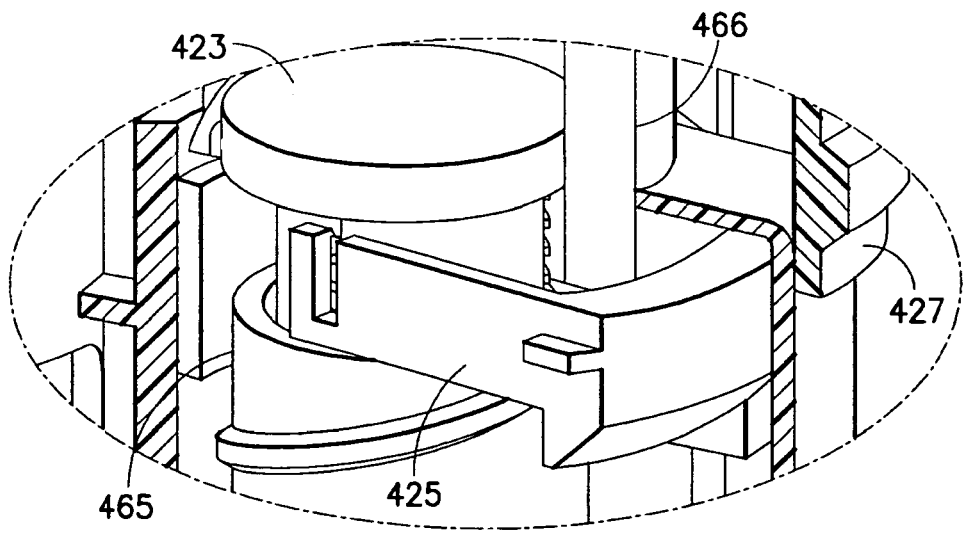
Figure 46:
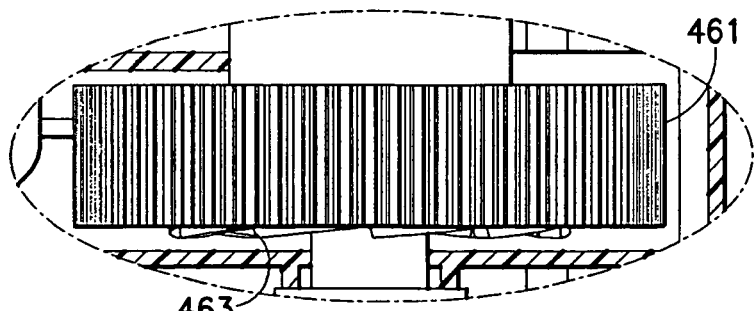
FIGS. 45-49 illustrate delivering the dose with the drug delivery device of FIG. 13.
Figure 38:
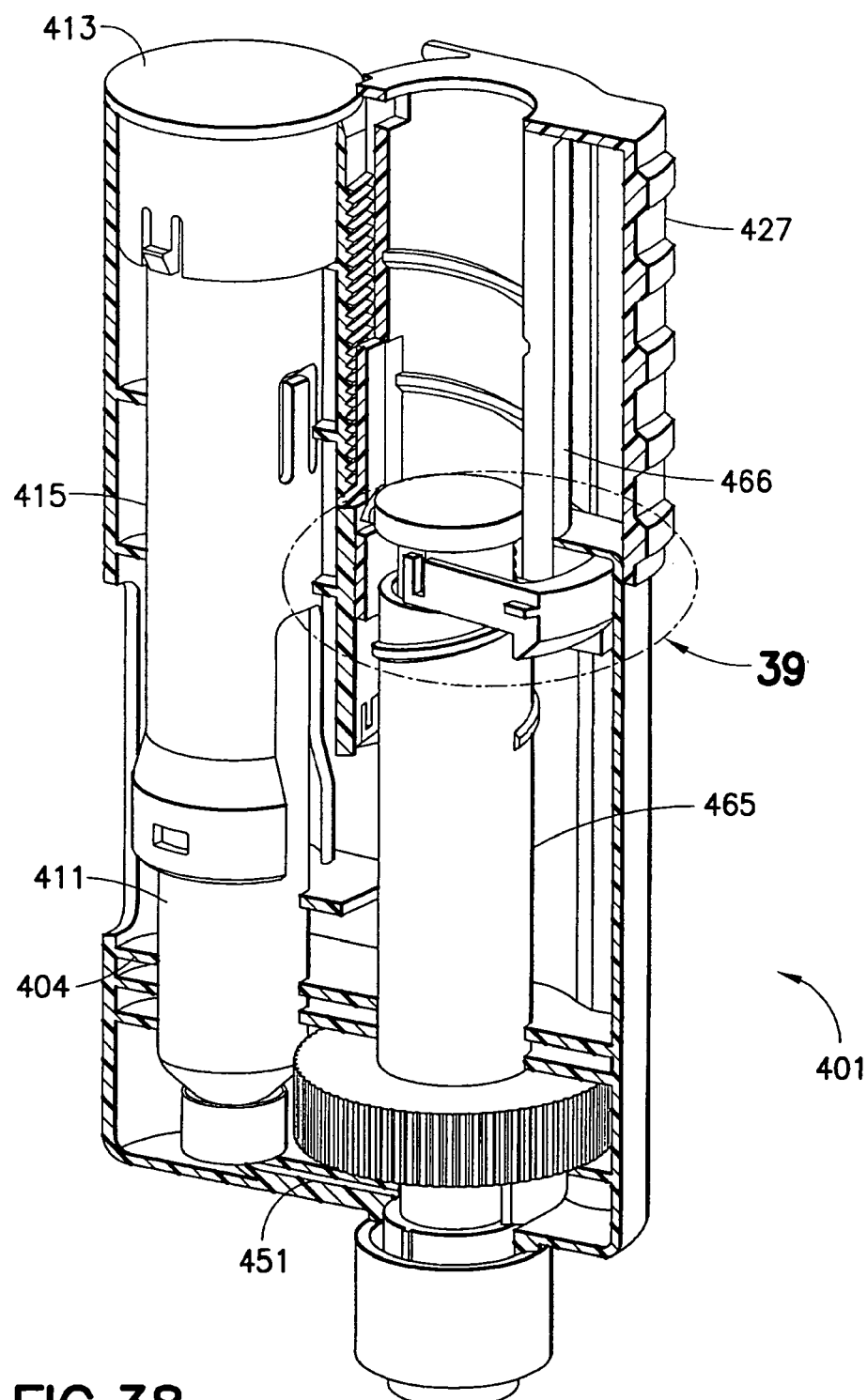

FIGS. 36-39 illustrate filling of the second chamber 421. A ratchet arm 425 holds the plunger 423 in place, as shown in FIGS. 36 and 37. The ratchet arm 425 engages teeth 424 of the plunger 423, as shown in FIG. 37. Pushing a fill button 427 inwardly disengages the ratchet arm 425 from the teeth 424 of the plunger 423, as shown in FIG. 39, thereby allowing the second chamber 421 to fill with medicament supplied through conduit 451 from the first chamber 491 of the cartridge 411 and the plunger 423 to move upwardly, as shown in FIG. 38.

Figure 40:
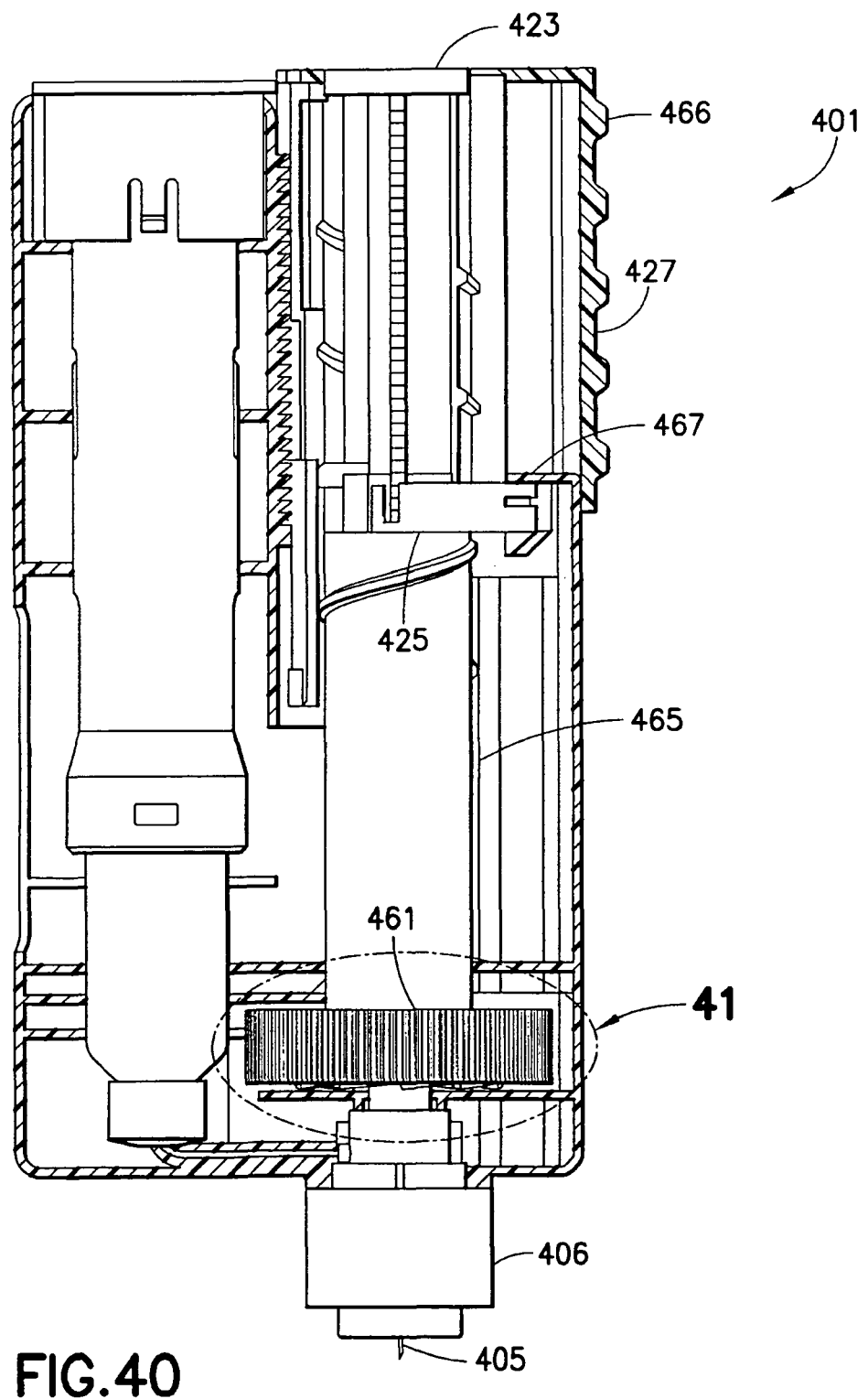
FIGS. 40-44 illustrate operation of the dose setting of the drug delivery device of FIG. 13.
Figure 41:
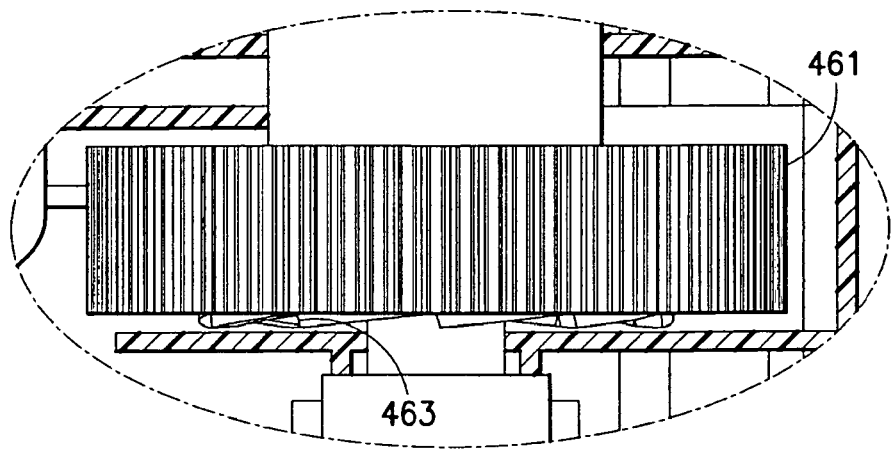
Figure 43:
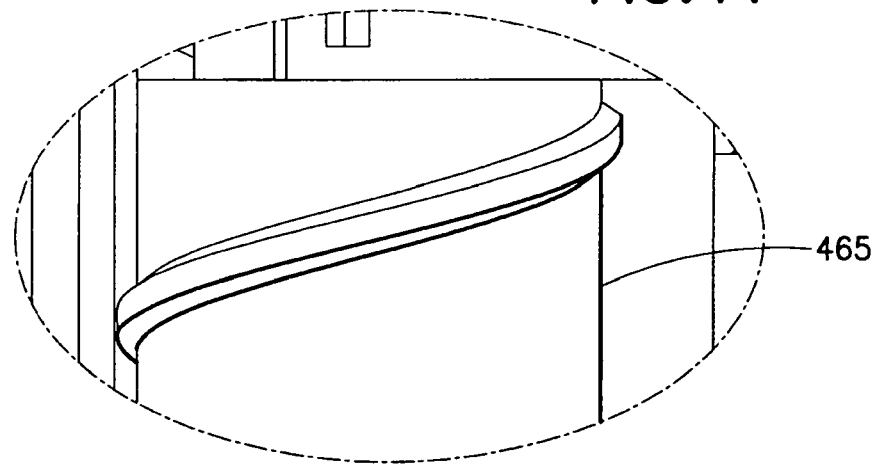
Figure 44:
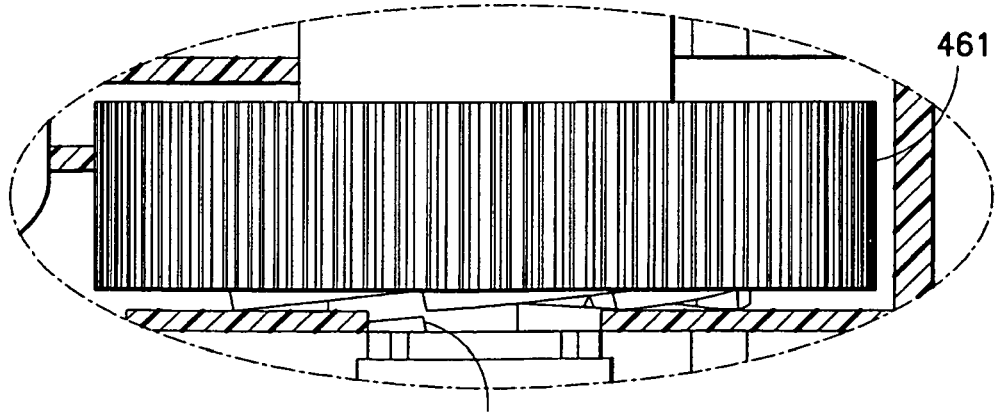
Figure 42:
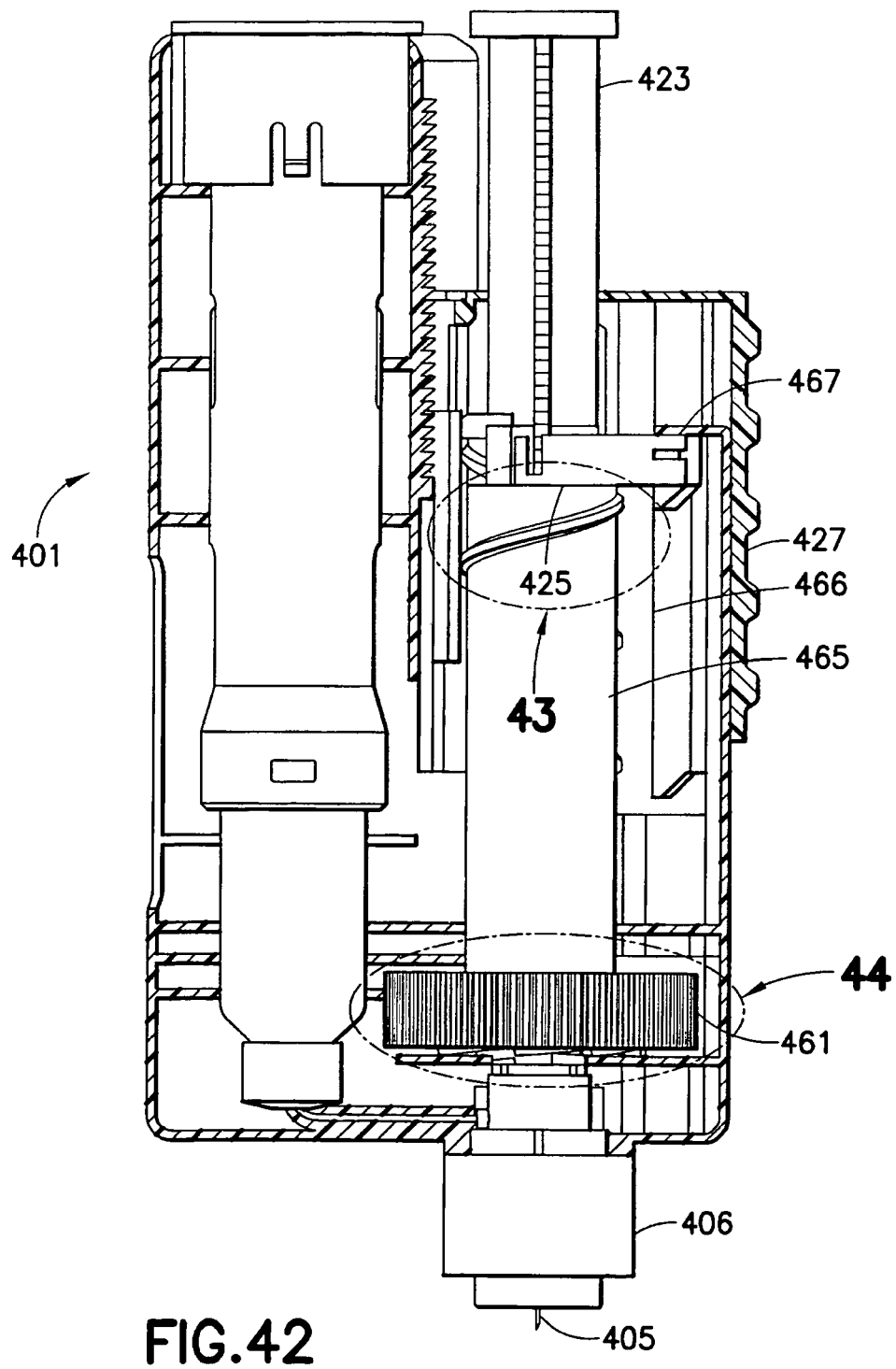

FIGS. 40-44 illustrate setting a dose with the drug delivery device 401. As shown in FIGS. 40 and 41, a clutch 463 engages a dose setting member or wheel 461 to prevent slippage of the dose setting wheel 461 during an injection. The clutch 463 prevents the dose setting wheel 461 from being rotated. As shown in FIGS. 42 and 43, the clutch 463 disengages the dose setting wheel 461 for dialing a medicament dose by separating the dose setting wheel 461 from the clutch 463, as shown in FIGS. 42 and 44. Rotating the dose wheel 461 rotates the lead screw 465, which in turn moves the dose slider 466 to the desired level. As shown in FIG. 40, the dose slider 466 is lifted to a first position with the plunger 423 when the medicament fills the second chamber 421. The dose setting wheel 461 is then rotated to move the dose slider to a second position corresponding to the desired medicament dose. To fully inject the full medicament dose in the second chamber 421, the dose slider is moved to a position in which the dose slider 466 abuts a lip 467 of the device housing 403. A medicament dose less than a full dose results in the dose slider 466 being set at a position between the housing lip 467 and the top of the plunger 423, as shown in FIG. 42. To correct a set medicament dose, the dose setting wheel 461 is separated from the clutch 463 and the dose slider 466 is moved to the correct dose setting. Furthermore, when no medicament is remaining in the first chamber 491 of the cartridge 411, the plunger 423 does not lift when depressing the cartridge button 413 to fill the second chamber 421, thereby indicating the absence of sufficient medicament to deliver a medicament dose.

Figure 45:
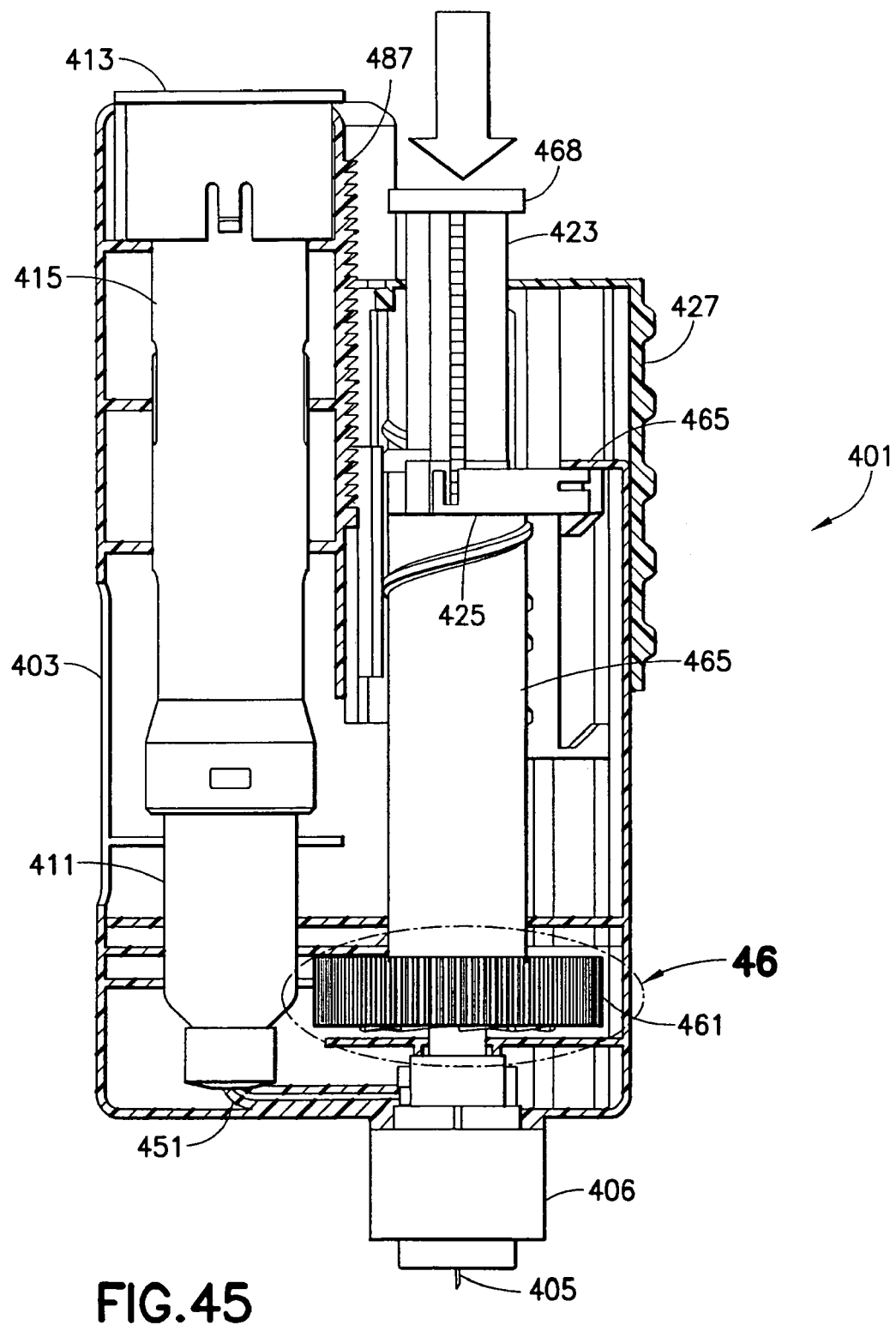

FIGS. 45-49 illustrate the operation of delivering a dose. The plunger 423 is pushed downwardly to deliver the medicament dose. The clutch 463 engages the dose setting wheel 461 to prevent movement of the dose setting wheel, thereby preventing the amount of the medicament dose delivered from changing. The injection stops when the plunger button 468 abuts the dose slider 466, as shown in FIG. 45, thereby having delivered the set medicament dose.

Figure 47:
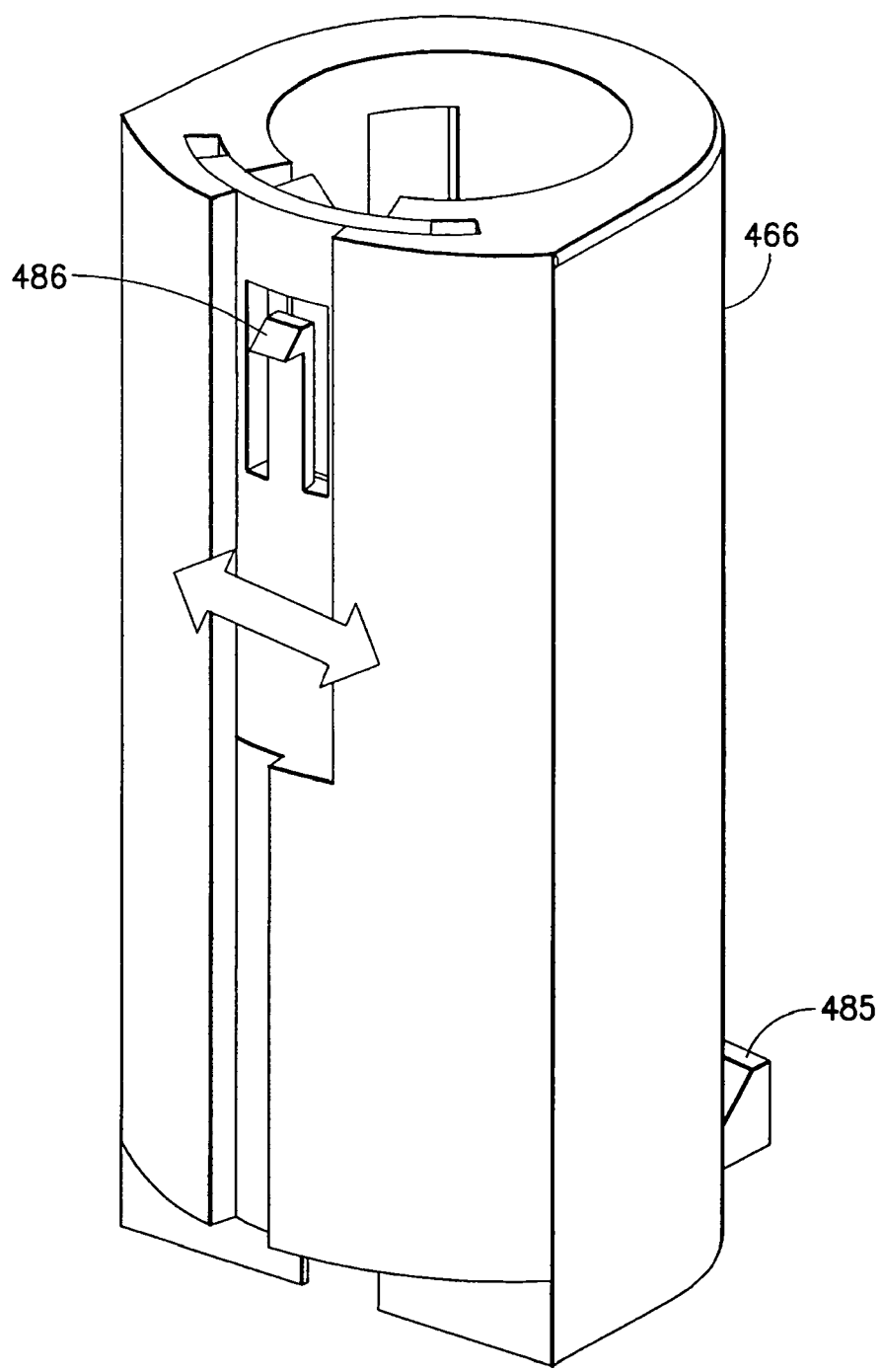
Figure 48:
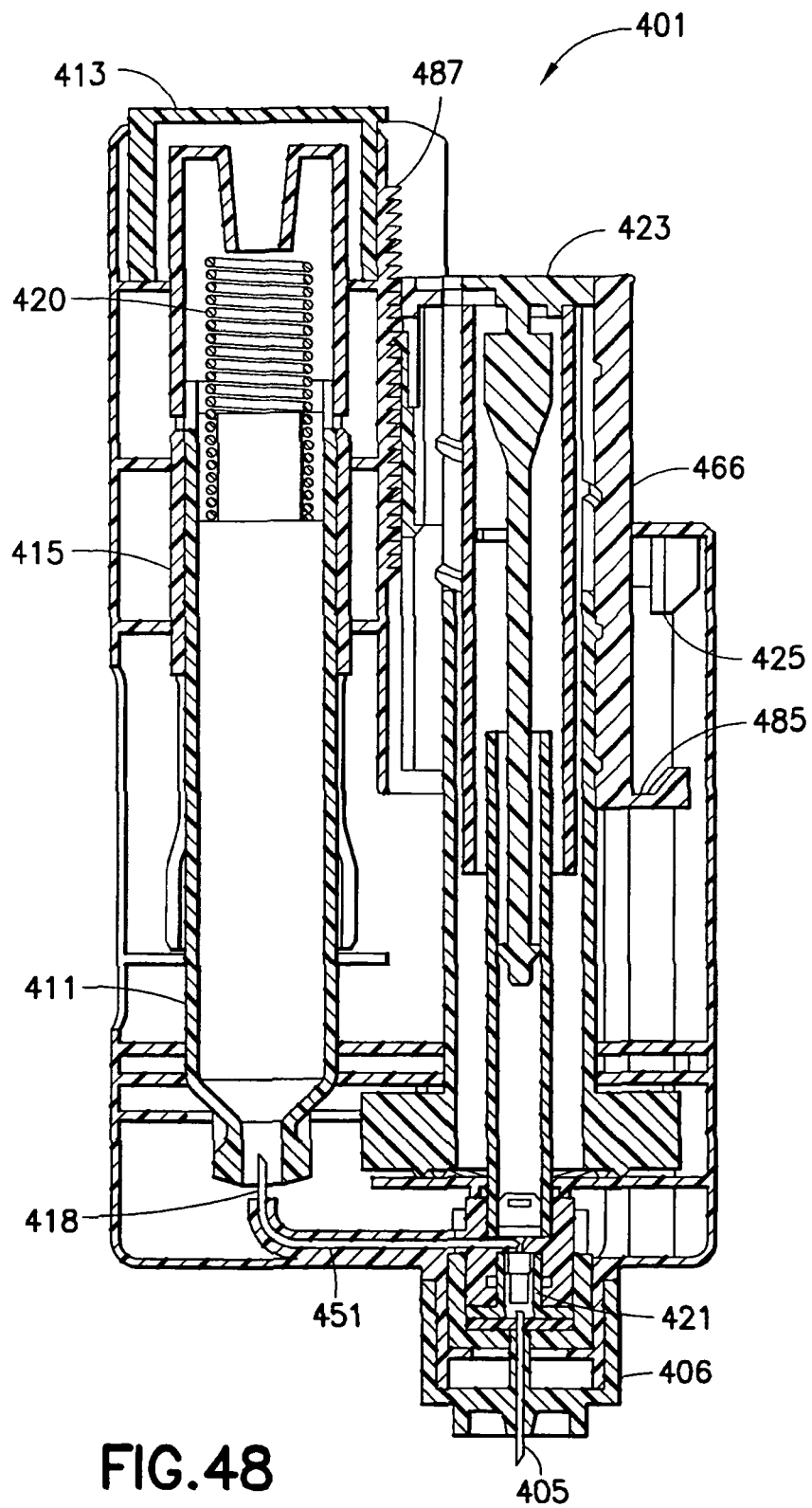
Figure 49:
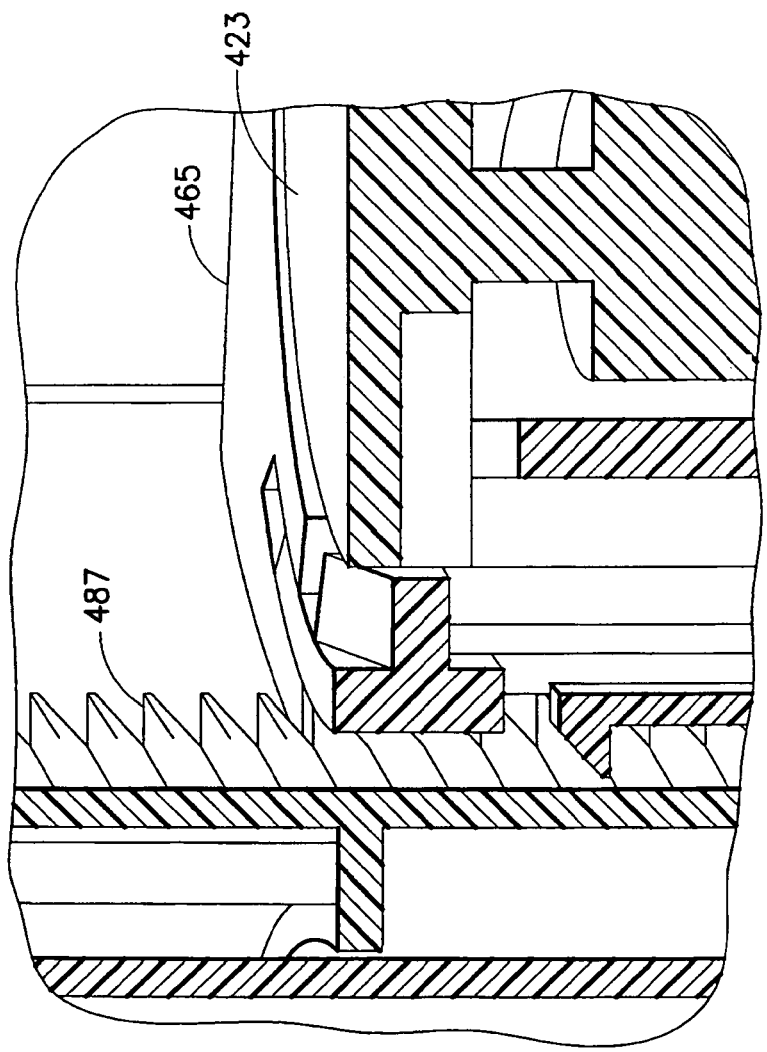

A hook 485 of the dose slider 466 engages the ratchet arm 425 to limit upper movement of the dose slider 466, as shown in FIG. 40. The dose slider 466 has a locking arm 486 that engages teeth 487 that allows for upward movement of the dose slider 466 and prevents downward movement of the dose slider 466. The dose slider 466 is flexible/collapsible, as shown in FIG. 47, to disengage the locking arm 486 from the teeth 487 to allow the dose slider 466 to be moved downwardly to set the medicament dose.

Alternatively, the drug delivery device according to exemplary embodiments of the present invention can be used as a reconstituting drug delivery system. The first chamber contains a diluent. The second chamber, which can be removable/replaceable, contains a solid drug. Accordingly, the drug delivery device enables a reconstitution or resuspension system. The first chamber can store sufficient diluent for many injections, and the second chamber can store a solid drug for fewer injections, such as one or two. Accordingly, the drug delivery device according to exemplary embodiments of the present invention can be used as a reconstitution system, including as a reconstitution system for high pressure injections.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

The invention claimed is:

1. A dual-chambered drug delivery device, comprising:
a first chamber in which a medicament is stored;
a dose setting member for setting a medicament dose, said dose setting member being rotatable to set the medicament dose, said dose setting member not being axially moveable with respect to said first chamber;
a spring that is configured to apply a force to a stopper in said first chamber;
a second chamber in fluid communication with said first chamber, the medicament dose being transferred to said second chamber from said first chamber upon application of said force from said spring prior to injecting the medicament dose; and
a needle communicating with said second chamber for injecting the medicament dose into an injection site;
wherein a central longitudinal axis of said dose setting member is collinear with a central longitudinal axis of said second chamber; and
a central longitudinal axis of said first chamber is substantially parallel to and offset from said central longitudinal axis of said second chamber.

2. The dual-chambered drug delivery device according to claim 1, wherein
a first central longitudinal axis through said needle is parallel to and spaced from a second central longitudinal axis through said first chamber.

3. The dual-chambered drug delivery device according to claim 1, wherein
said second chamber has a smaller cross sectional area than said first chamber.

4. The dual-chambered drug delivery device according to claim 1, wherein
said central longitudinal axis of said dose setting member is substantially parallel to a central longitudinal axis through said needle.

5. A dual-chambered drug delivery device, comprising:
a first chamber in which a medicament is stored;
a dose setting member for setting a medicament dose, said dose setting member being rotatable to set the medicament dose, said dose setting member not being axially moveable;
a second chamber in fluid communication with said first chamber, the medicament dose being transferred to said second chamber from said first chamber prior to injecting the medicament dose;
a needle communicating with said second chamber for injecting the medicament dose into an injection site;
a plunger rod gear disposed on a plunger rod; and
a cam wheel gear connected to said dose setting member and rotatably engaged with said plunger rod gear such that rotation of said dose setting member rotates said cam wheel gear and rotation of said cam wheel gear rotates said plunger rod gear, and rotation of said plunger rod gear moves said plunger rod from a first position to a second position; wherein
a central longitudinal axis of said first chamber is substantially parallel to and offset from said central longitudinal axis of said second chamber.

6. A dual-chambered drug delivery device, comprising:
a cartridge having a first chamber in which a medicament is stored;
a spring that is configured to apply a force to a stopper in said first chamber;
a second chamber in fluid communication with said first chamber, a central longitudinal axis of said first chamber being substantially parallel to and offset from a central longitudinal axis of said second chamber, a portion of a medicament dose being transferred to said second chamber from said first chamber upon application of said force from said spring prior to injecting the medicament dose;
a dose setting member for setting the medicament dose, the medicament dose being equal to or less than the portion of the medicament transferred to said second chamber, a central longitudinal axis of said dose setting member being collinear with said central longitudinal axis of said second chamber, said dose setting member not being axially moveable with respect to said first chamber; and
a needle communicating with said second chamber for injecting the medicament dose into an injection site.

7. The dual-chambered drug delivery device according to claim 6, wherein
said second chamber has a smaller cross sectional area than said first chamber.

8. The dual-chambered drug delivery device according to claim 6, wherein
a first valve regulates flow of the medicament between said first chamber and said second chamber; and
a second valve regulates flow of the medicament dose between said second chamber and said needle.

9. The dual-chambered drug delivery device according to claim 8, wherein
said first valve comprises a flap or disk valve.

10. The dual-chambered drug delivery device according to claim 8, wherein
said second valve comprises a pressure relief valve.

11. The dual-chambered drug delivery device according to claim 6, wherein
a plunger rod is moved when the medicament portion is transferred to said second chamber.

12. The dual-chambered drug delivery device according to claim 11, wherein
rotation of said dose setting member moves a dose slider from a first position flush with a free end of said plunger rod to a second position corresponding to the medicament dose to be delivered.

13. A dual-chambered drug delivery device, comprising:
a cartridge having a first chamber in which a medicament is stored;
a second chamber in fluid communication with said first chamber, a central longitudinal axis of said first chamber being substantially parallel to and offset from a central longitudinal axis of said second chamber, a portion of a medicament dose being transferred to said second chamber from said first chamber prior to injecting the medicament dose;
a dose setting member for setting the medicament dose, the medicament dose being equal to or less than the portion of the medicament transferred to said second chamber, a central longitudinal axis of said dose setting member being collinear with said central longitudinal axis of said second chamber;
a needle communicating with said second chamber for injecting the medicament dose into an injection site;
a plunger rod that moves when the medicament portion is transferred to said second chamber; and
a clutch that engages said dose setting member to prevent rotation of said dose setting member when the medicament dose is not being set; wherein
rotation of said dose setting member moves a dose slider from a first position flush with a free end of said plunger rod to a second position corresponding to the medicament dose to be delivered.

14. A dual-chambered drug delivery device, comprising:
a cartridge having a first chamber in which a medicament is stored;
a second chamber in fluid communication with said first chamber, a central longitudinal axis of said first chamber being substantially parallel to and offset from a central longitudinal axis of said second chamber, a portion of a medicament dose being transferred to said second chamber from said first chamber prior to injecting the medicament dose;
a dose setting member for setting the medicament dose, the medicament dose being equal to or less than the portion of the medicament transferred to said second chamber, a central longitudinal axis of said dose setting member being collinear with said central longitudinal axis of said second chamber;
a needle communicating with said second chamber for injecting the medicament dose into an injection site;
a plunger rod that moves when the medicament portion is transferred to said second chamber; and
a ratchet arm that engages said plunger rod to prevent movement of said plunger rod, thereby preventing the medicament portion from being transferred to said second chamber.

15. A method of injecting medicament using a dual-chambered drug delivery device, comprising the steps of:
storing a medicament in a first chamber;
compressing a spring to apply a force to a stopper in said first chamber;
transferring a portion of the medicament from the first chamber to a second chamber upon application of said force from said spring, a central longitudinal axis of said first chamber being substantially parallel to and offset from a central longitudinal axis of said second chamber;
setting a medicament dose to be injected by a dose setting member, a central longitudinal axis of said dose setting member being collinear with said central longitudinal axis of said second chamber, said dose setting member not being axially moveable with respect to said first chamber; and
injecting the set medicament dose from the portion of the medicament in the second chamber into an injection site.

16. The method of injecting medicament using a dual-chambered drug delivery device according to claim 15, wherein
the set medicament dose is less than or equal to the portion of the medicament dose in the second chamber.

17. The method of injecting medicament using a dual-chambered drug delivery device according to claim 15, further comprising
tracking the amount of the medicament stored in the first chamber.

18. The method of injecting medicament using a dual-chambered drug delivery device according to claim 17, further comprising
preventing the medicament dose from being set when the stored medicament being tracked is less than a predetermined amount.

* * * * *